(12) United States Patent
Kim et al.

(10) Patent No.: US 8,173,273 B2
(45) Date of Patent: May 8, 2012

(54) ANTHRACENE DERIVATIVES, METHOD FOR PREPARATION THEREOF, AND ORGANIC ELECTRONIC DEVICE USING THE SAME

(75) Inventors: Ji-Eun Kim, Daejeon Metropolitan (KR); Kong-Kyeom Kim, Daejeon Metropolitan (KR); Tae-Yoon Park, Daejeon Metropolitan (KR); Hye-Young Jang, Daejeon Metropolitan (KR); Jae-Chol Lee, Daejeon Metropolitan (KR); Sung-Kil Hong, Daejeon Metropolitan (KR); Dong-Seob Jeong, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 264 days.

(21) Appl. No.: 12/226,487

(22) PCT Filed: Apr. 20, 2007

(86) PCT No.: PCT/KR2007/001939
§ 371 (c)(1),
(2), (4) Date: Oct. 20, 2008

(87) PCT Pub. No.: WO2007/123339
PCT Pub. Date: Nov. 1, 2007

(65) Prior Publication Data
US 2010/0044681 A1      Feb. 25, 2010

(30) Foreign Application Priority Data

Apr. 21, 2006  (KR) .................. 10-2006-0036239

(51) Int. Cl.
*H01L 51/54* (2006.01)

(52) U.S. Cl. .... 428/690; 428/917; 257/40; 257/E51.026; 257/E51.052; 313/504; 313/505; 313/506; 564/426; 564/424

(58) Field of Classification Search ............ 428/690, 428/917; 257/40, E51.026, E51.052; 313/504, 313/505, 506; 556/465; 564/426, 434
See application file for complete search history.

(56) References Cited

U.S. PATENT DOCUMENTS 5,635,308 A * 6/1997 Inoue et al. .................. 428/696
(Continued)

FOREIGN PATENT DOCUMENTS

EP    0681019 A2    11/1995
(Continued)

OTHER PUBLICATIONS

Danel et. al., Blue Emitting Anthracenes . . . Diarylamines, 2002, Chemical Materials, vol. 14, pp. 3860-3895.*
(Continued)

*Primary Examiner* — Jennifer Chriss
*Assistant Examiner* — Gregory Clark
(74) *Attorney, Agent, or Firm* — McKenna Long & Aldridge LLP

(57) ABSTRACT

The present invention relates to a novel anthracene derivative, a method for preparation thereof, and an organic electronic device using the same. The anthracene derivative according to the present invention can function as a hole injecting, hole transporting, electron injecting, electron transporting, or light emitting in an organic electronic device including an organic light emitting device, and in particular, used alone as a light emitting, or as a host or dopant in a host/dopant system. The organic electronic device according to the present invention exhibits excellent characteristics in terms of efficiency, drive voltage, life time, and stability.

9 Claims, 1 Drawing Sheet

U.S. PATENT DOCUMENTS

2005/0260442 A1  11/2005  Yu et al.

FOREIGN PATENT DOCUMENTS

| JP | 11111460 A | 4/1999 |
| JP | 16059535 A | 2/2004 |
| WO | WO 0172673 A1 | 10/2001 |
| WO | WO 0214244 A1 | 2/2002 |

OTHER PUBLICATIONS

Thompson et al., Asymmetric Triarlamines as Thermally Stable Hole Transporting Layers of Organic Light Emitting Devices, 1998, Chemical Materials, vol. 10, pp. 2235-2250.*

* cited by examiner

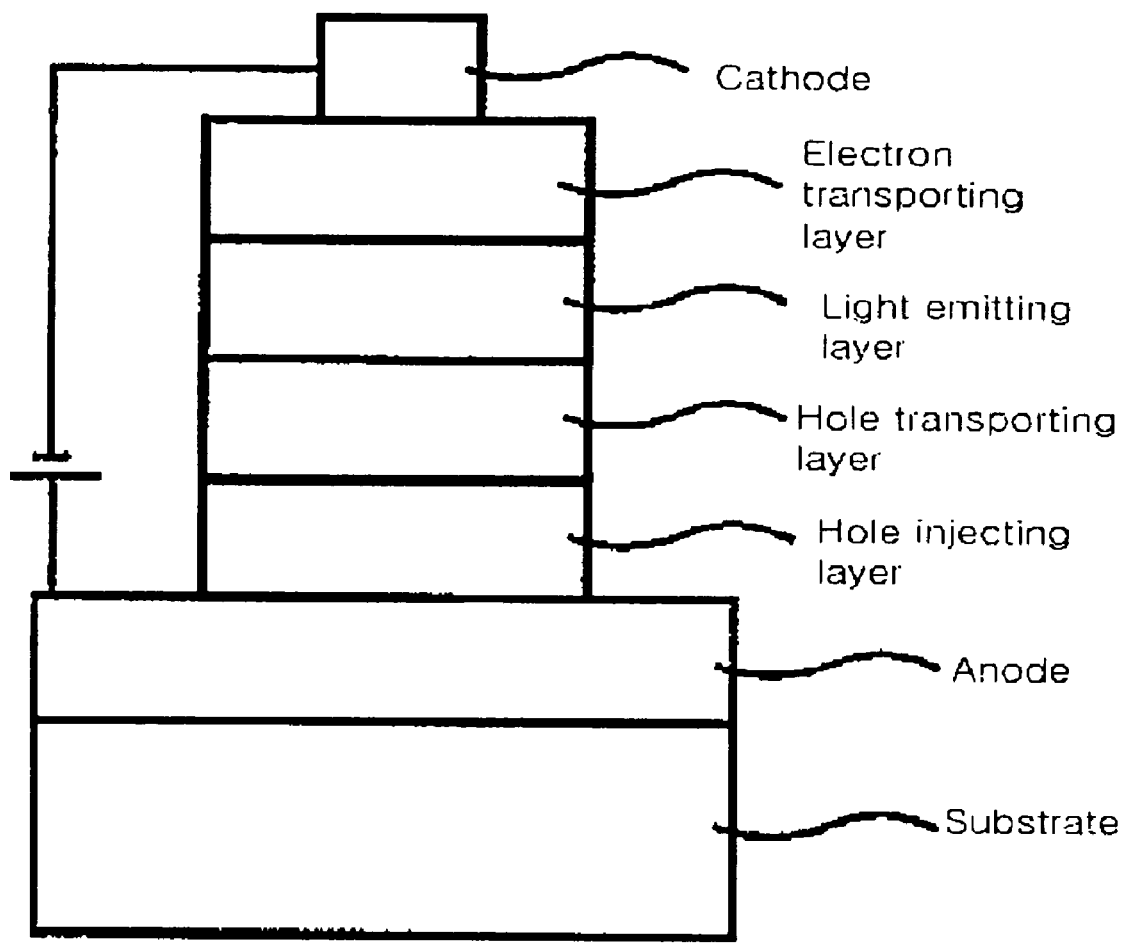

ANTHRACENE DERIVATIVES, METHOD FOR PREPARATION THEREOF, AND ORGANIC ELECTRONIC DEVICE USING THE SAME

This application is an application based on International Patent Application No. PCT/KR2007/001939 filed Apr. 20, 2007, which claims the benefit of Korean Application No. 10-2006-0036239 filed Apr. 21, 2006, which are hereby incorporated by reference for all purposes as if fully set forth herein.

TECHNICAL FIELD

The present invention relates to a novel anthracene derivative, a method for preparation thereof, and an organic electronic device using the same.

The present application claims the benefit of Korean Patent Application No. 2006-0036239 (filed on Apr. 21, 2006), which is incorporated herein by its entirety for reference.

BACKGROUND ART

The organic electronic device refers to a device which requires charge exchange between an electrode and an organic material using holes and electrons. The organic electronic device can be largely classified into two types according to its operation principle as follows. One type is an electronic device having a configuration in which an exciton is formed in an organic material layer by photons flown from an external light source into the device and the exciton is separated into an electron and a hole, the formed electron and hole are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC), and an organic transistor, which all require a hole injecting or hole transporting material, an electron injecting or electron transporting material, or a light emitting material for driving the device.

Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, a hole injecting layer, a hole transporting layer, a light emitting layer, an electron transporting layer, an electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast, and high-speed response.

The materials used for the organic material layer of the organic light emitting device can be classified into a light emitting material and a charge transporting material, for example, a hole injecting material, a hole transporting material, an electron transporting material, and an electron injecting material, according to their functions. The light emitting material can be classified into a high molecular weight type and a low molecular weight type, according to their molecular weight, and divided into a fluorescent material from singlet excited states and a phosphorescent material from triplet excited states according to their light emitting mechanism. Further, the light emitting material can be classified into a blue, green, or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE OF INVENTION

Technical Problem

The present inventors have synthesized a novel anthracene derivative, and have found that the anthracene derivative can be used as a hole injecting material, hole transporting material, electron injecting material, electron transporting material, or light emitting material, and in particular, that the anthracene derivative can be used alone as a light emitting material, or as a host or dopant in a host/dopant system, thereby exhibiting effects of increased efficiency, lower drive voltage, increased life-time, and higher stability of the organic electronic device. Based on these findings, they have completed the present invention.

Technical Solution

Therefore, it is an object of the present invention to provide a novel anthracene derivative, a method for preparation thereof, and an organic electronic device using the same.

Advantageous Effects

The anthracene derivative according to the present invention can function as a hole injecting, hole transporting, electron injecting, electron transporting, or light emitting in an organic electronic device including an organic light emitting device, and in particular, used alone as a light emitting, or as a host or dopant in a host/dopant system. The organic electronic device according to the present invention exhibits excellent characteristics in terms of efficiency, drive voltage, life time, and stability.

BRIEF DESCRIPTION OF THE DRAWINGS

FIG. 1 illustrates the structure of the organic light emitting device according to one embodiment of the present invention.

BEST MODE FOR CARRYING OUT THE INVENTION

The present invention provides an anthracene derivative represented by the following formula 1.

[Formula 1]

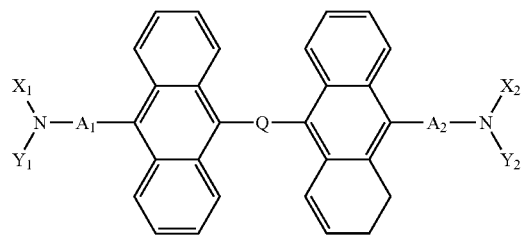

wherein $X_1$, $X_2$, $Y_1$, and $Y_2$ are the same or different from each other, and are each independently a $C_6$ to $C_{20}$ aryl group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_6$ to $C_{20}$ arylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkenyl group, a $C_3$ to $C_{20}$ cycloalkyl group, a $C_6$ to $C_{20}$ aryl group, a $C_5$ to $C_{20}$ heterocyclic group, —BRR', —SiRR'R", and —GeRR'R"; a $C_5$ to $C_{20}$ heterocyclic group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_6$ to $C_{20}$ arylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_5$ to $C_{20}$ heterocyclic group, —BRR', —SiRR'R", and —GeRR'R"; or a $C_2$ to $C_{20}$ alkylene group which is combined with a $C_6$ to $C_{20}$ aryl group to form a fused ring, wherein R, R' and R" are the same or different from each other, and are each independently hydrogen, a $C_1$ to $C_{20}$ alkyl group, a $C_3$ to $C_{20}$ cycloalkyl group, a $C_6$ to $C_{20}$ aryl group, or $C_5$ to $C_{20}$ heterocyclic group, and Q, $A_1$, and $A_2$ are the same or different from each other, and are each independently

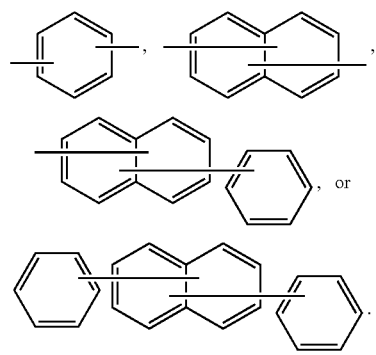

In the formula 1, $X_1$, $X_2$, $Y_1$, and $Y_2$ are the same or different from each other, and are preferably each independently phenyl, naphthyl, biphenyl, fluorenyl, anthracenyl, tetracenyl, pentacenyl, terphenyl, tetralinyl, stilbenyl, perylenyl, pyrenyl, phenanthrenyl, triphenylenyl, crycenyl, or pyridyl, which is unsubstituted or substituted with at least one selected from the group consisting of a $C_1$ to $C_{20}$ alkyl group, —SiRR'R", and —GeRR'R"; or a $C_2$ to $C_{20}$ alkylene group which is combined with phenyl or naphthyl to form a fused ring, wherein R, R' and R" are the same or different from each other, and are preferably each independently a $C_1$ to $C_{20}$ alkyl group.

Further, in the formula 1,

Q, $A_1$, and $A_2$ are the same or different from each other, and are preferably each independently a group selected from the group consisting of:

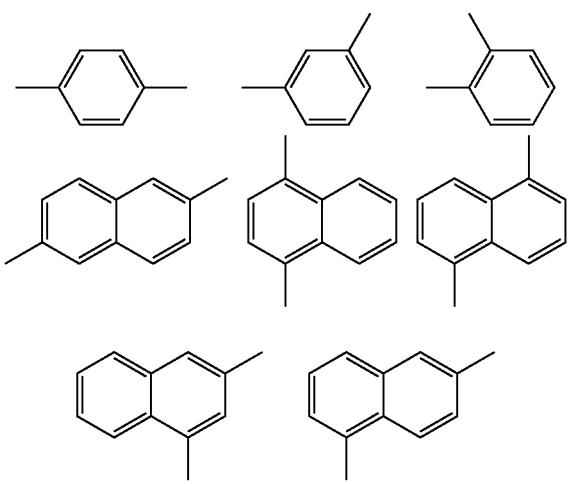

-continued
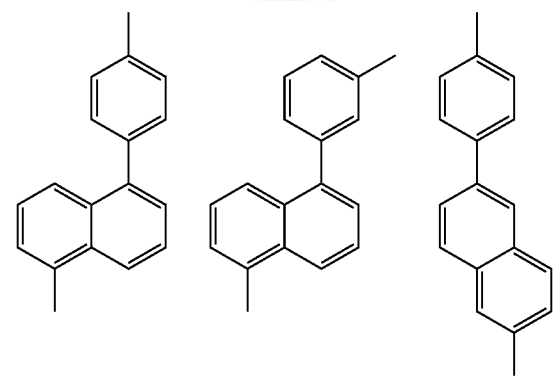
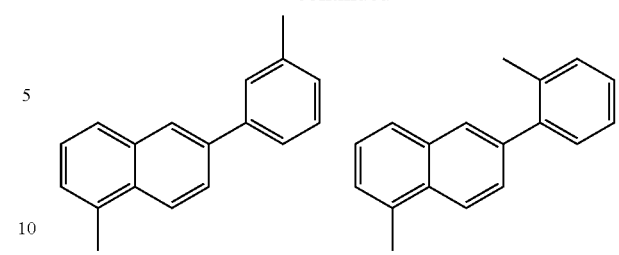
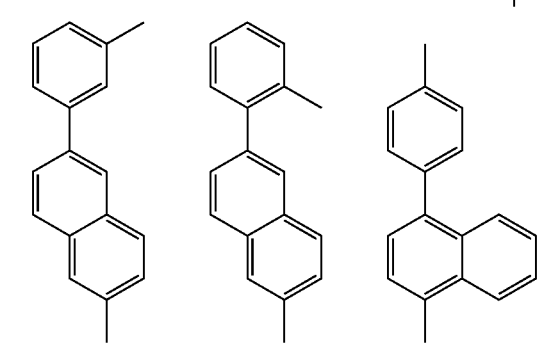
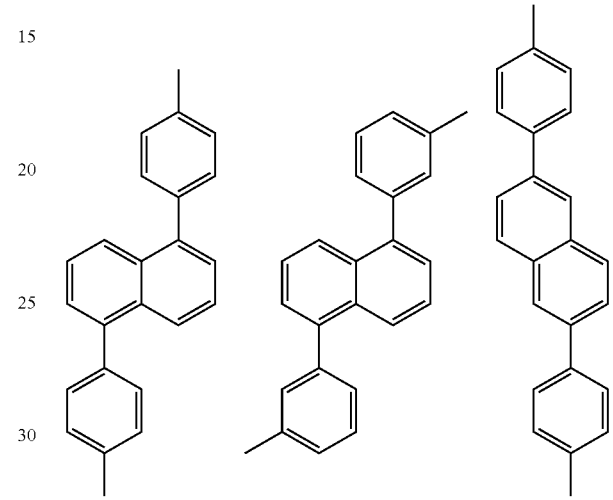
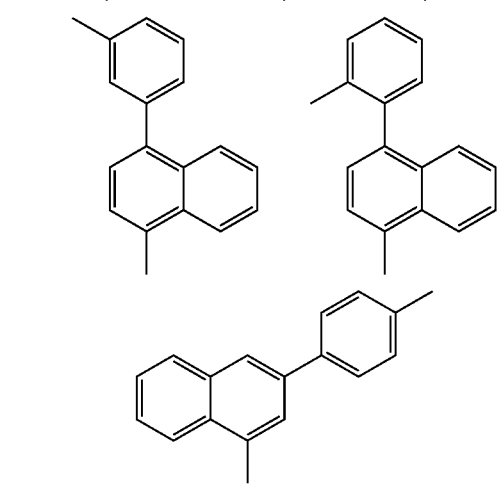
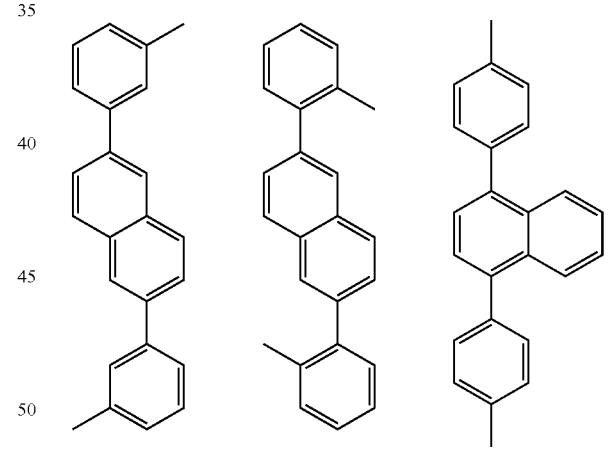
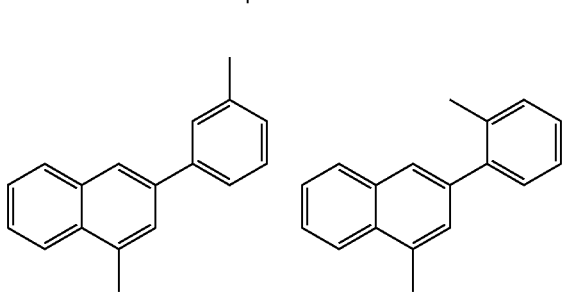
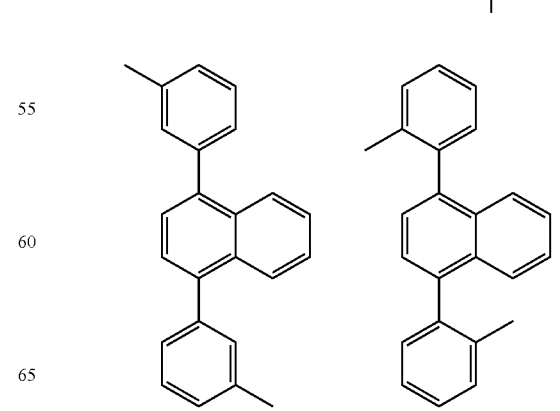
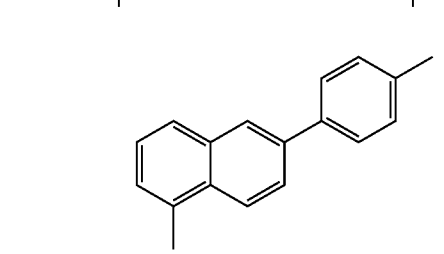

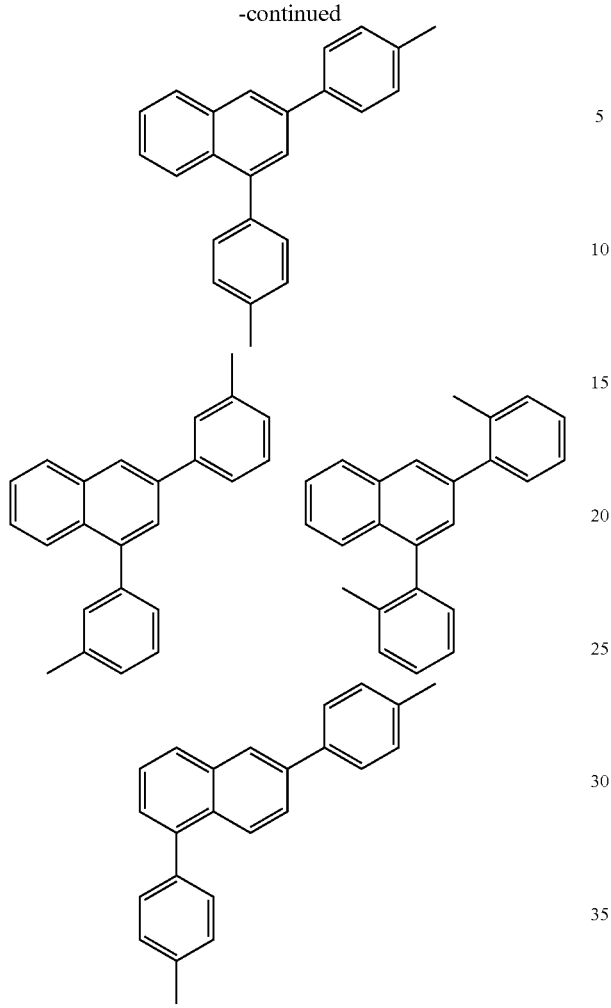
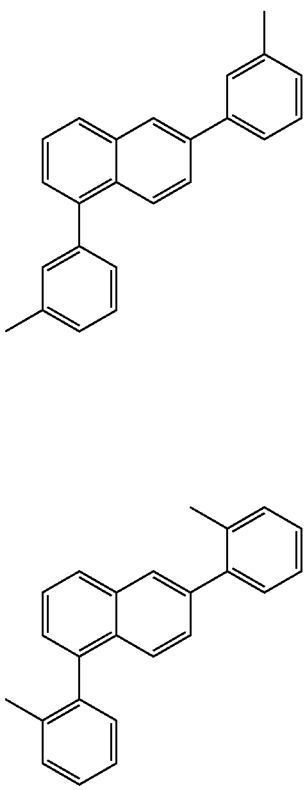
Specific examples of the compound of the formula 1 are shown below, but are not limited thereto.
[Compound 1]
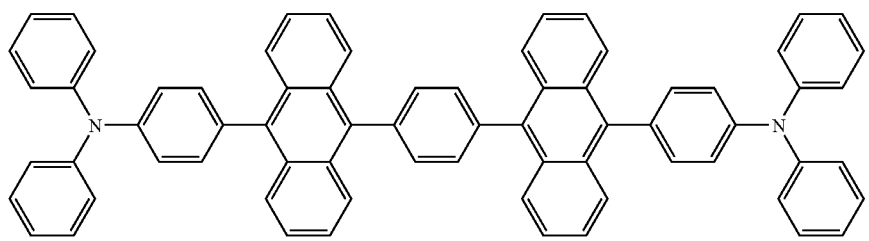
[Compound 2]
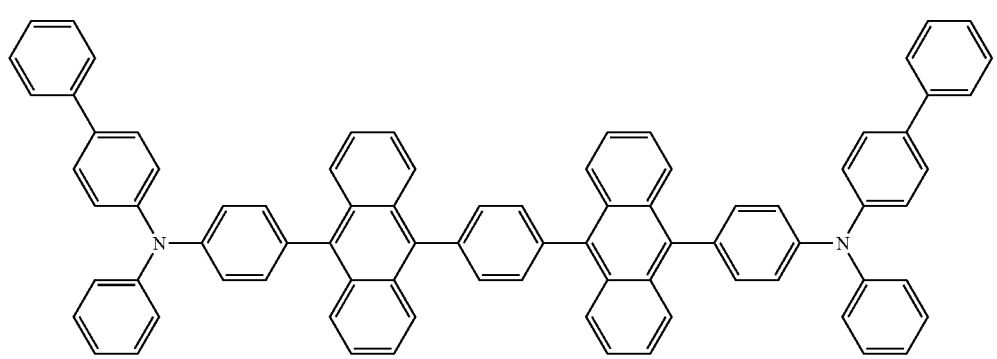

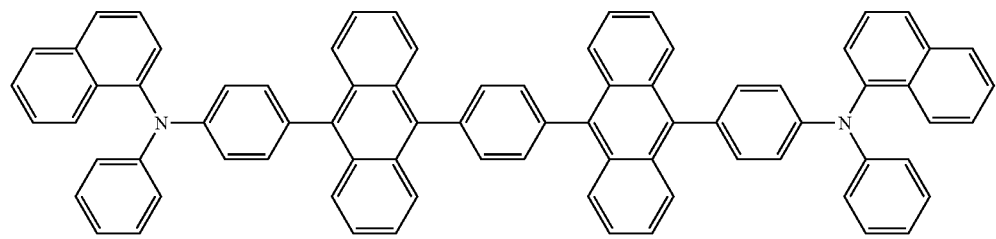
[Compound 3]
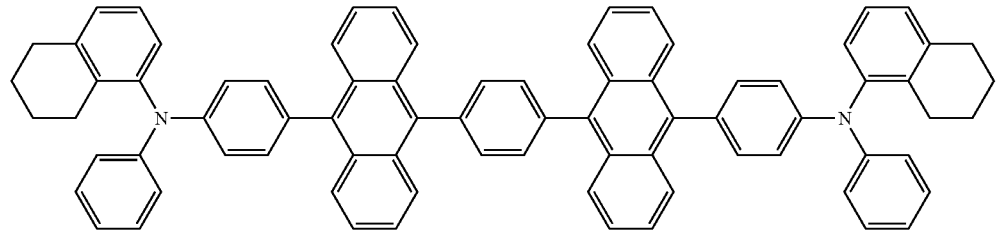
[Compound 4]
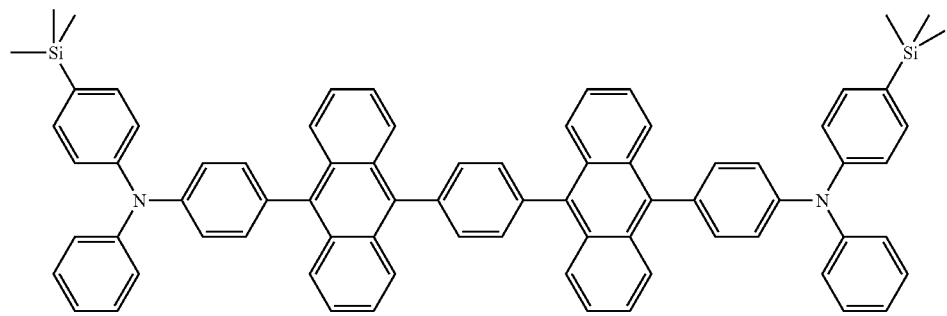
[Compound 5]
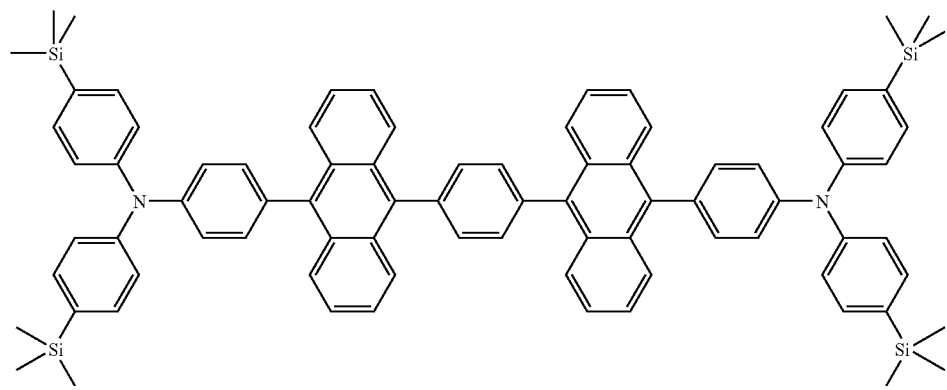
[Compound 6]
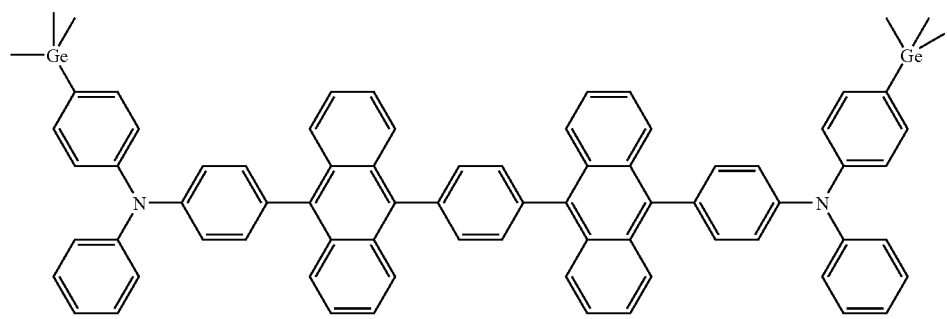
[Compound 7]

[Comound 8]
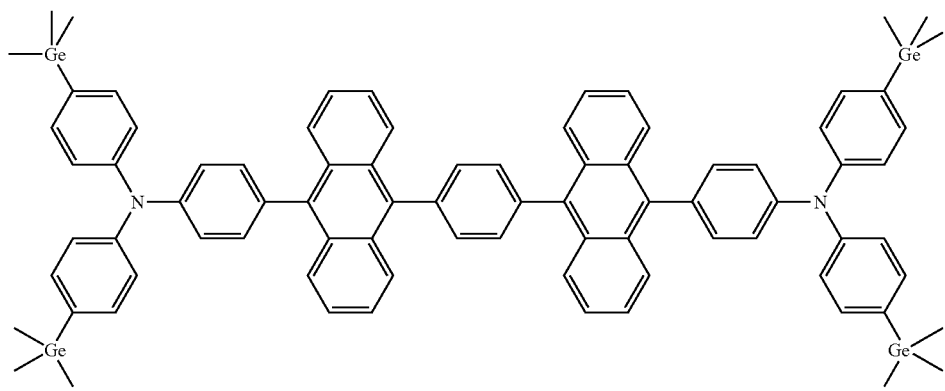
[Compound 9]
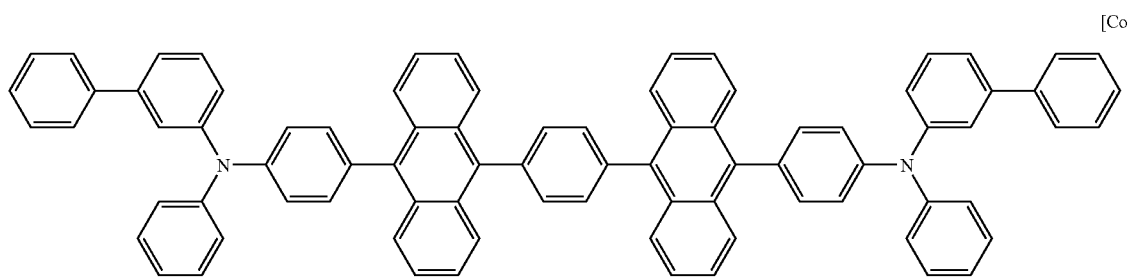
[Compound 10]
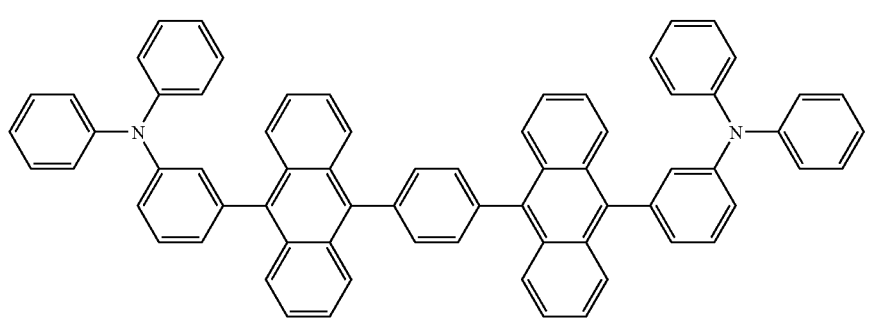
[Compound 11]
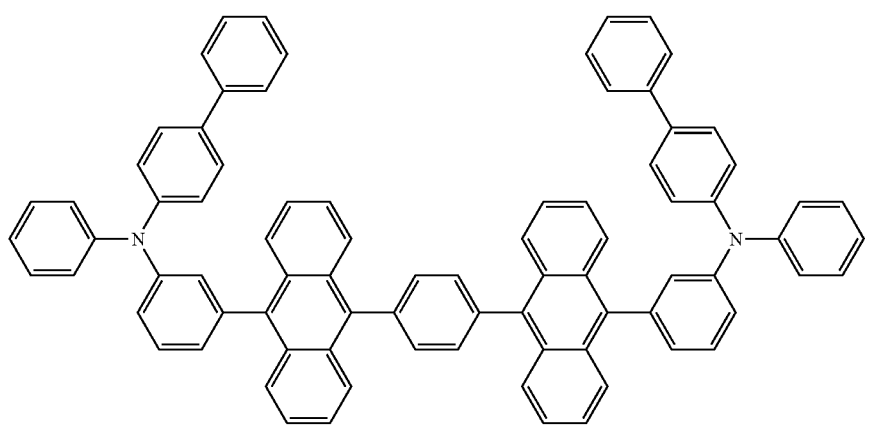

[Compound 12]
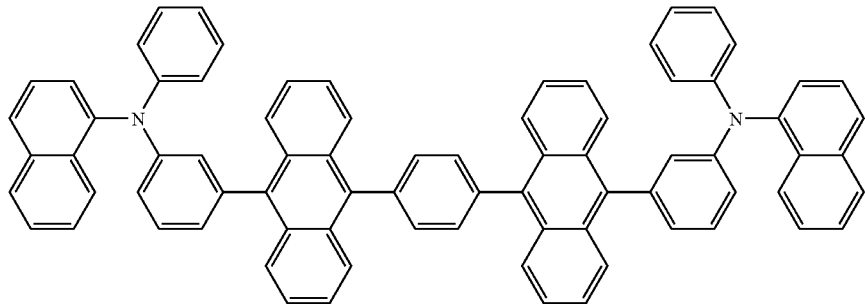
[Compound 13]
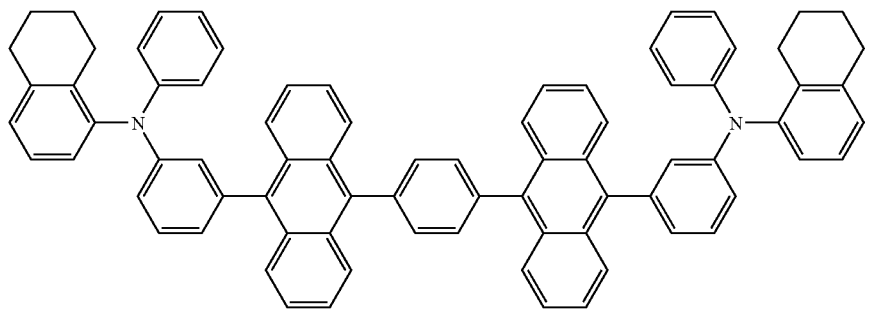
[Compound 14]
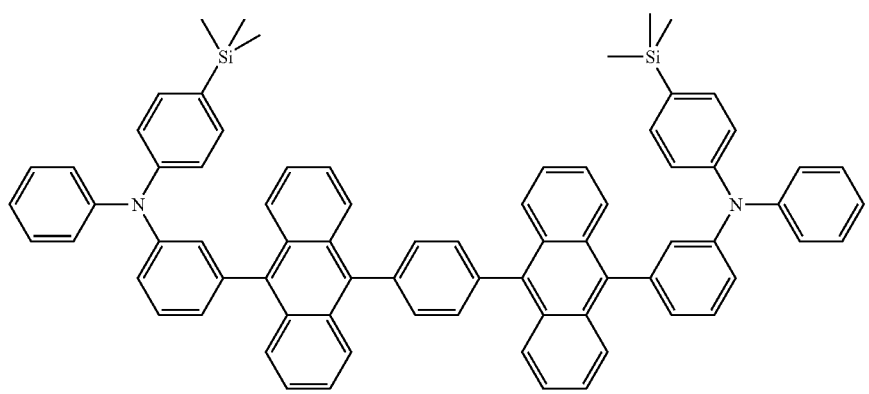
[Compound 15]
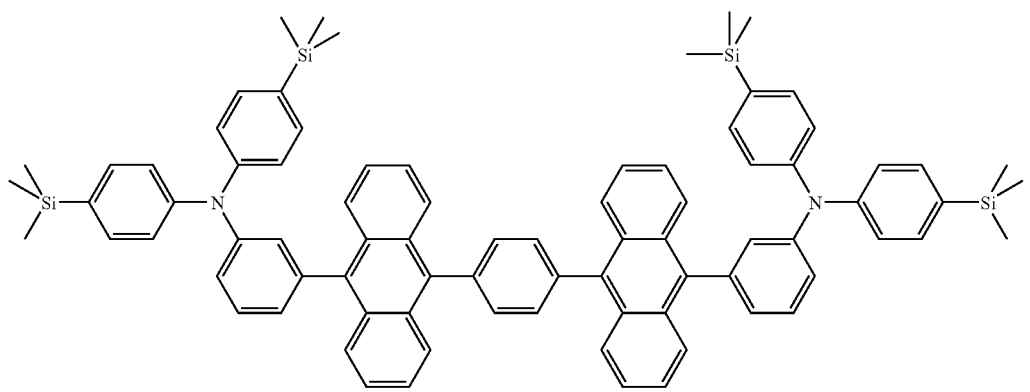

-continued
[Compound 16]
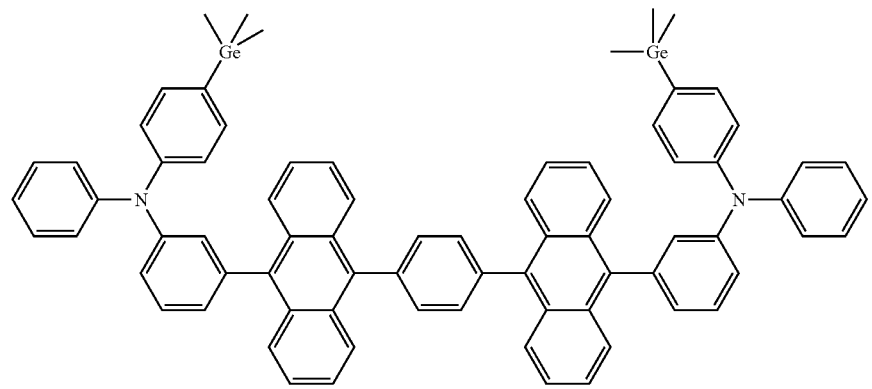
[Compound 17]
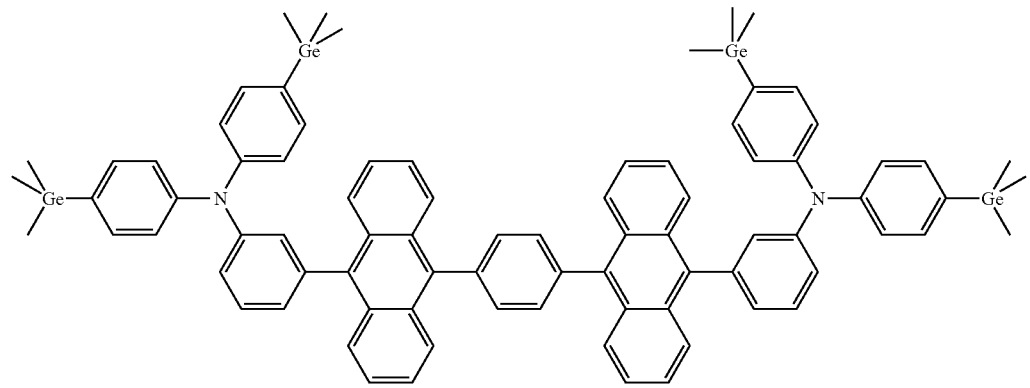
[Compound 18]
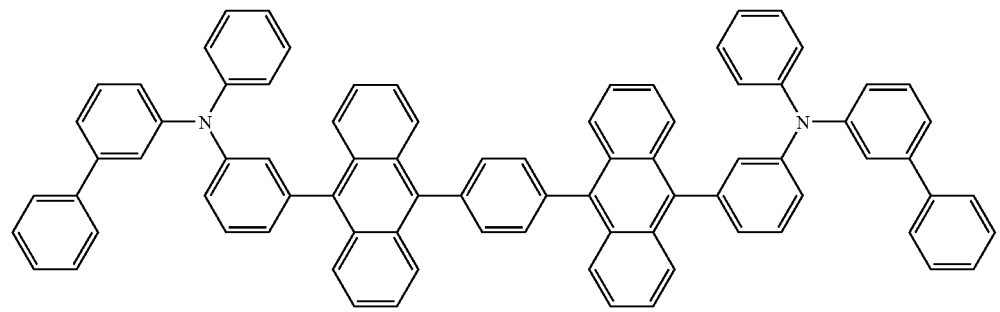
[Compound 19]
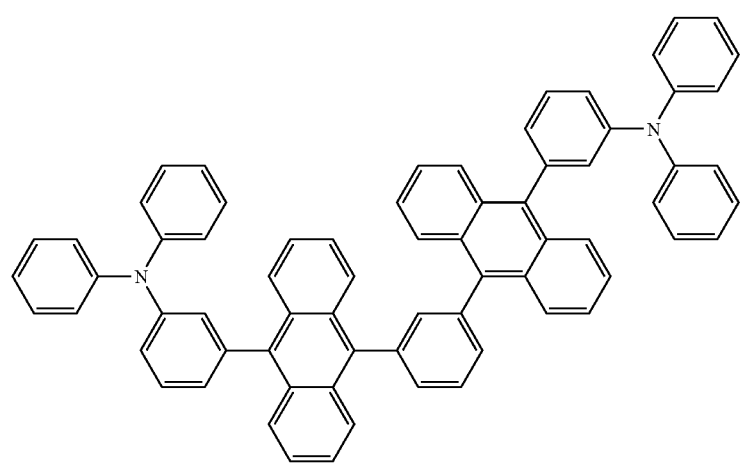

[Compound 20]
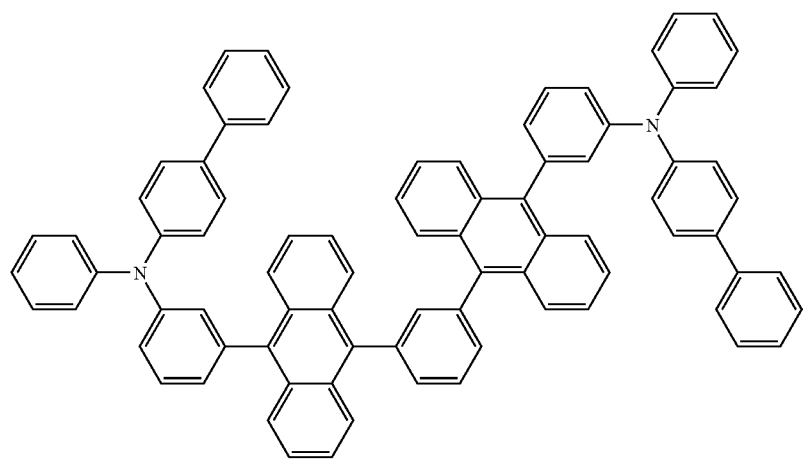
[Compound 21]
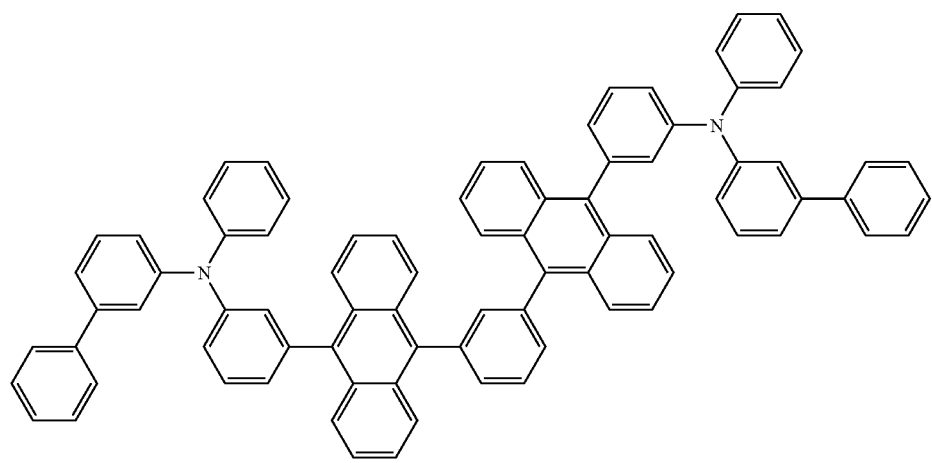
[Compound 22]
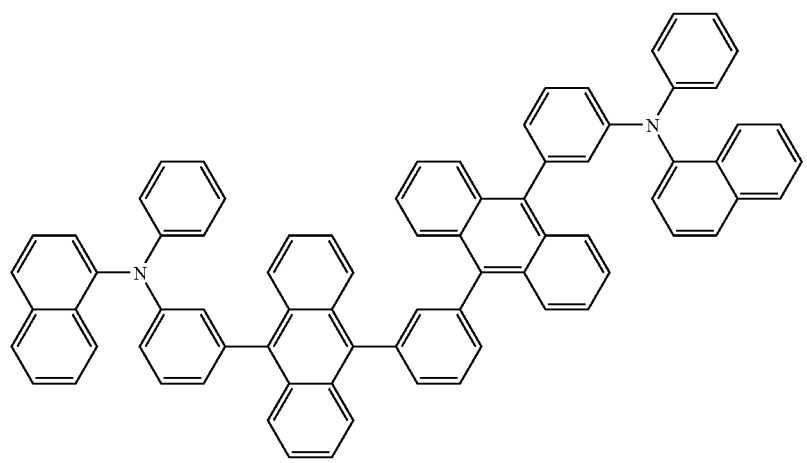

[Compound 23]
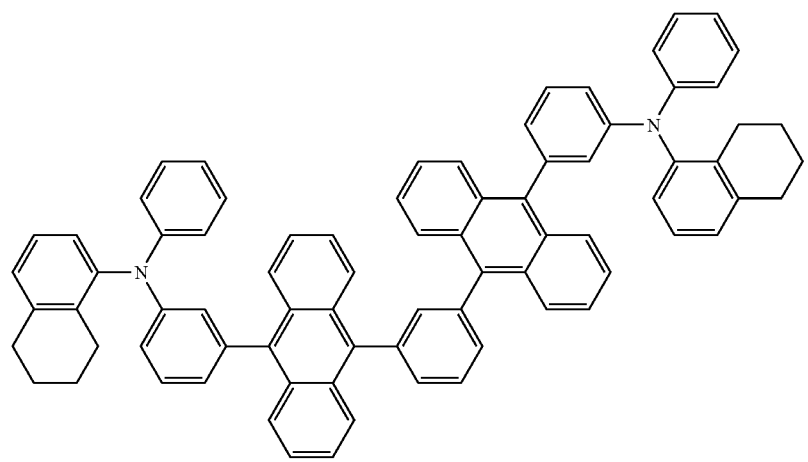
[Compound 24]
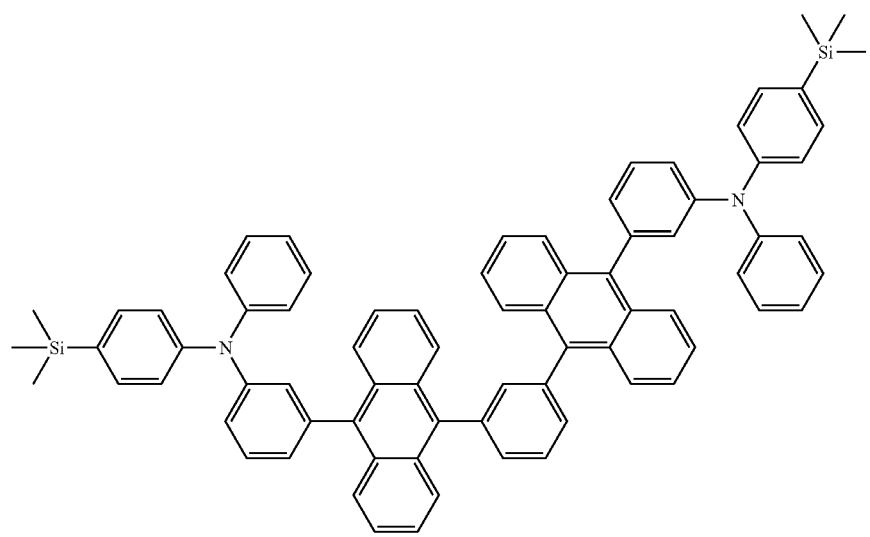
[Compound 25]
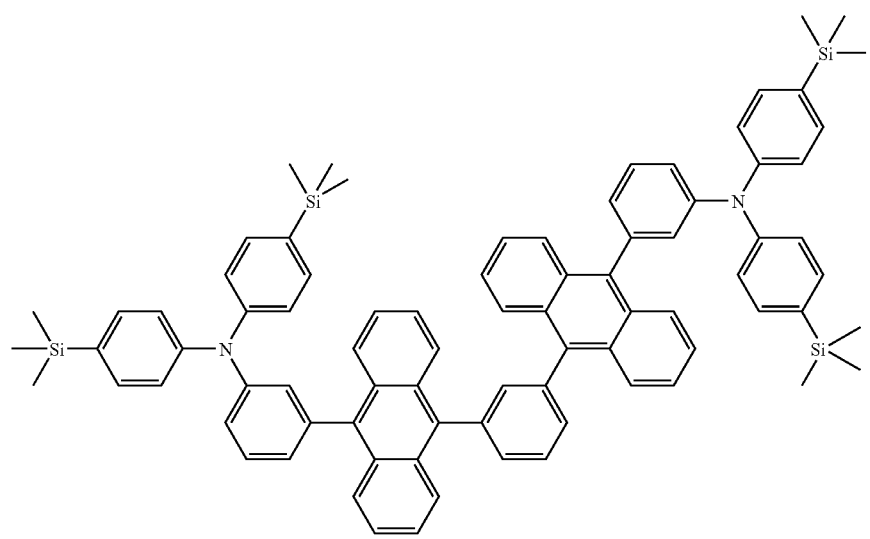

[Compound 26]
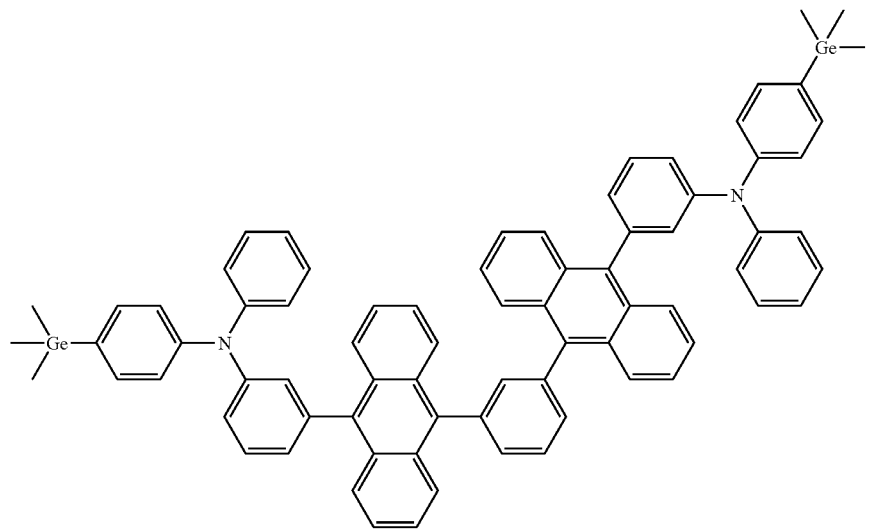
[Compound 27]
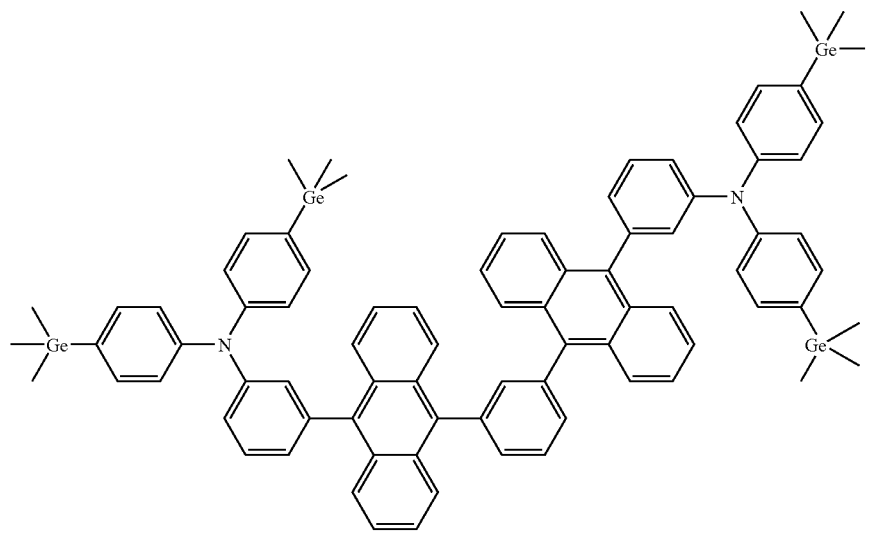
[Compound 28]
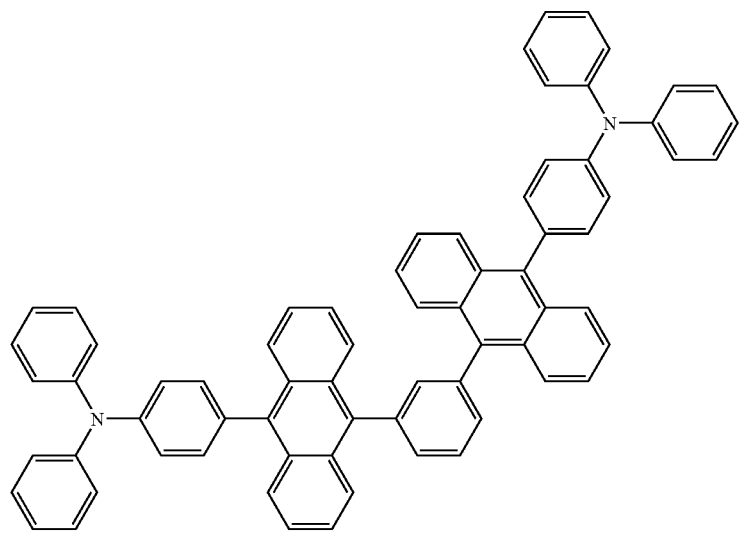

-continued
[Compound 29]
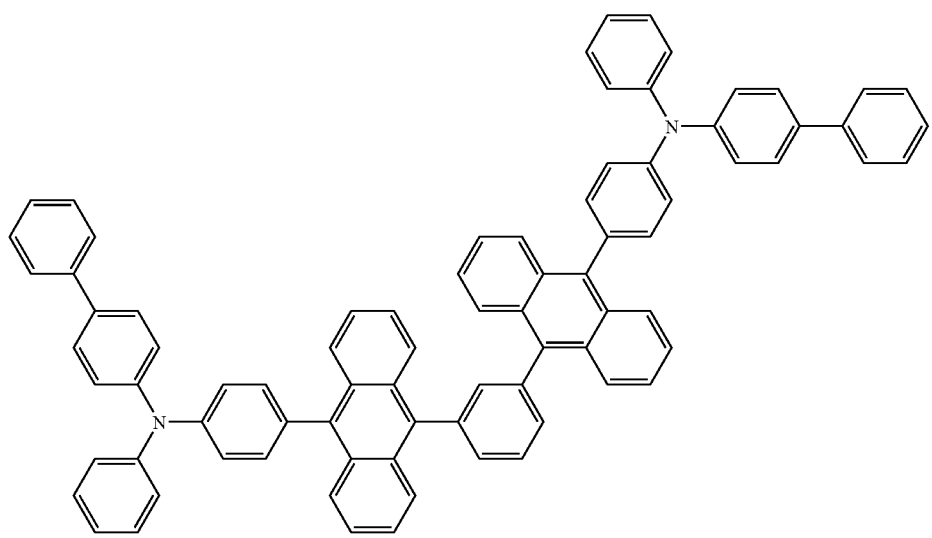
[Compound 30]
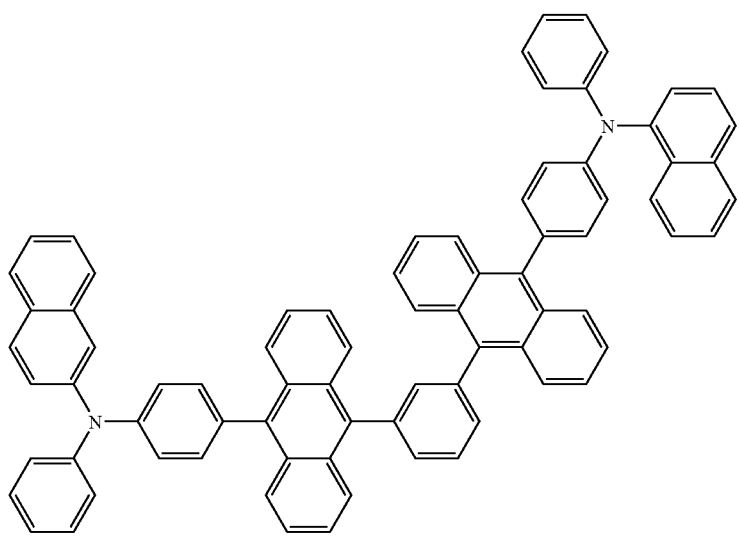
[Compound 31]
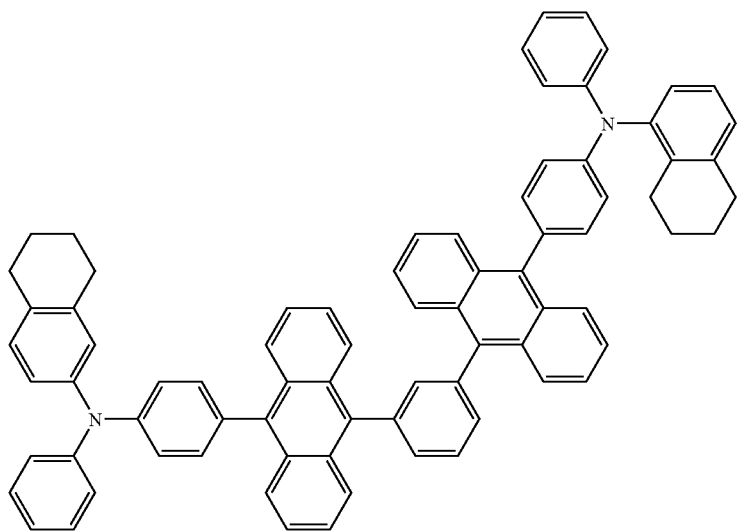

[Compound 32]
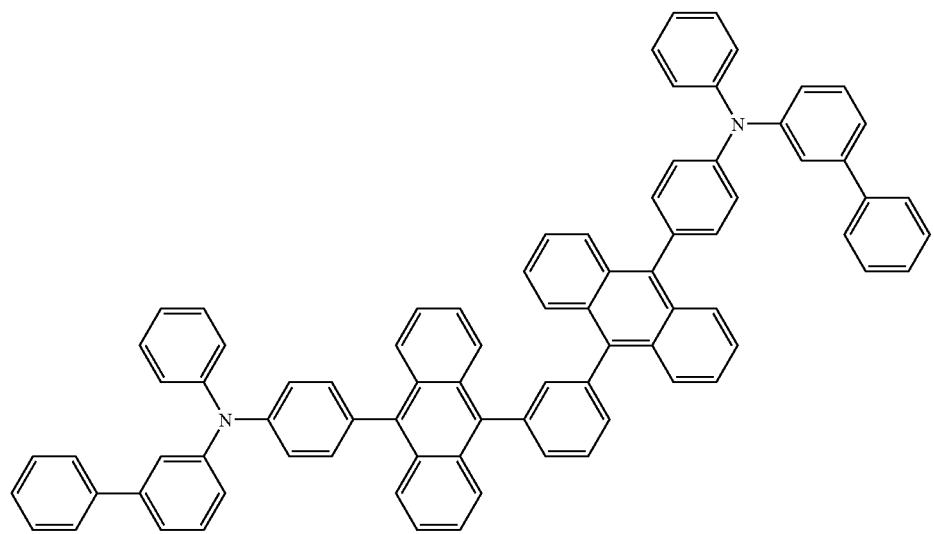
[Compound 33]
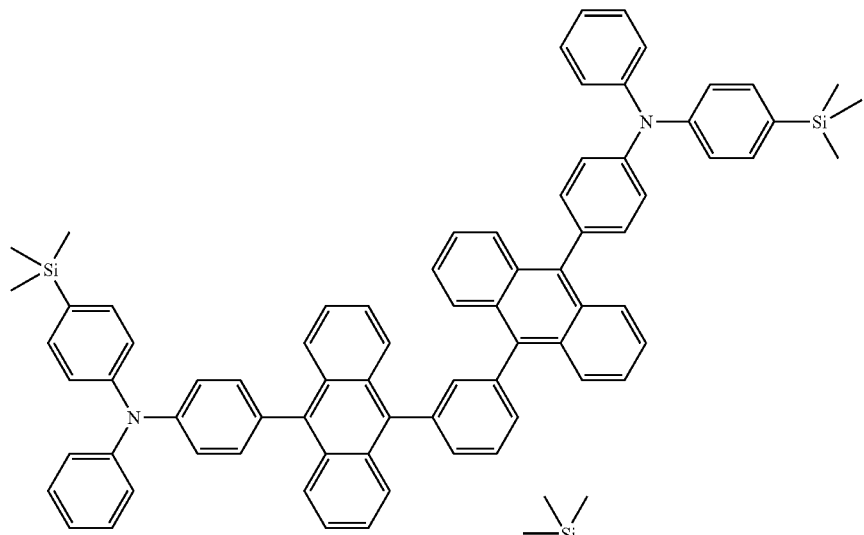
[Compound 34]
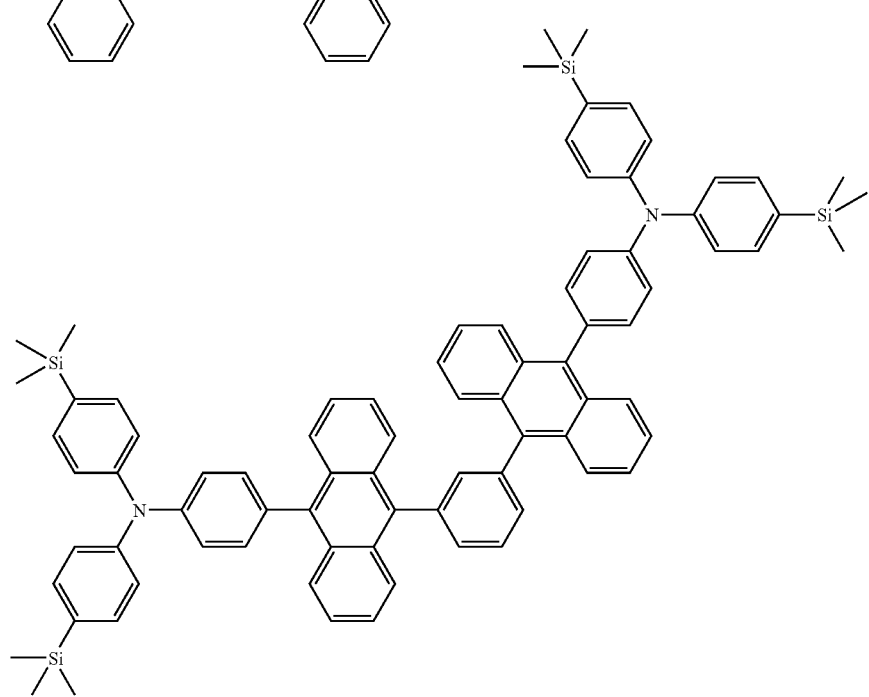

[Compound 35]
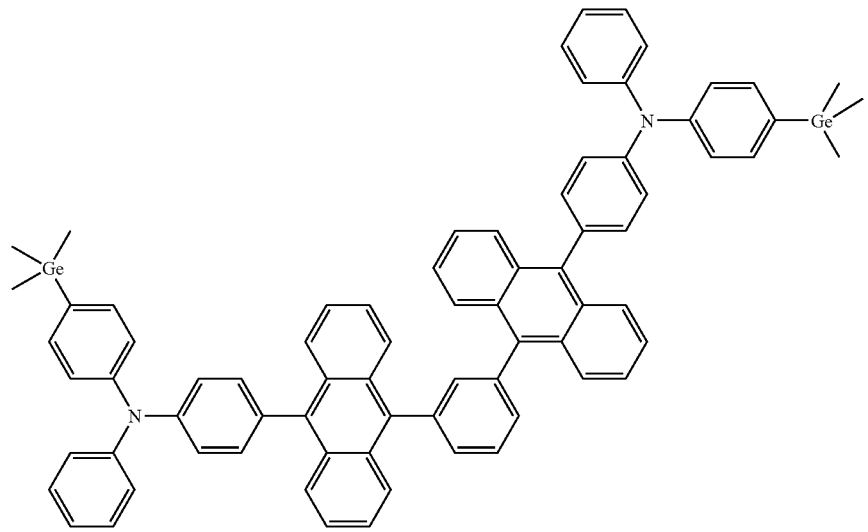
[Compound 36]
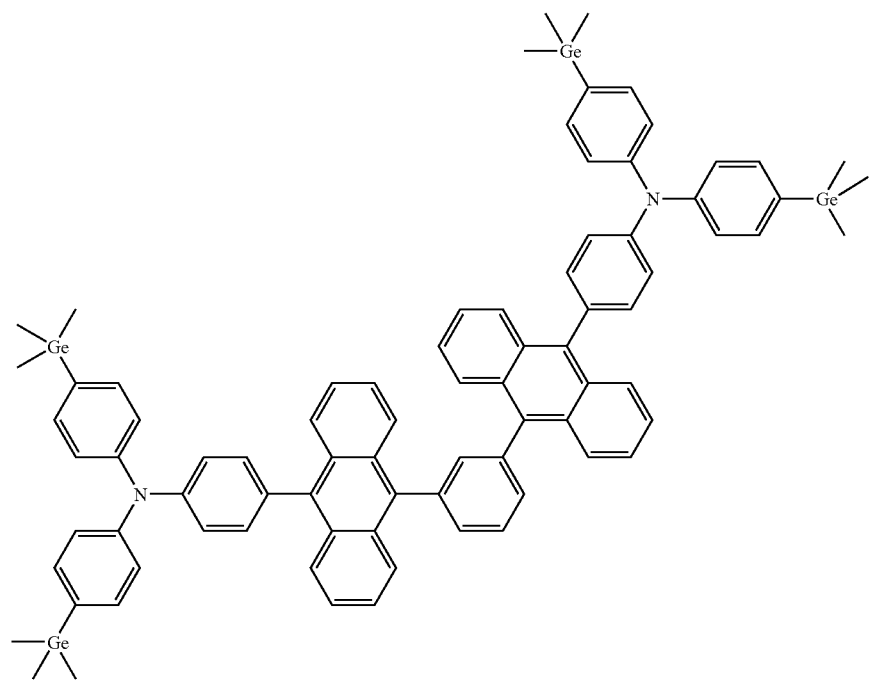
[Compound 37]
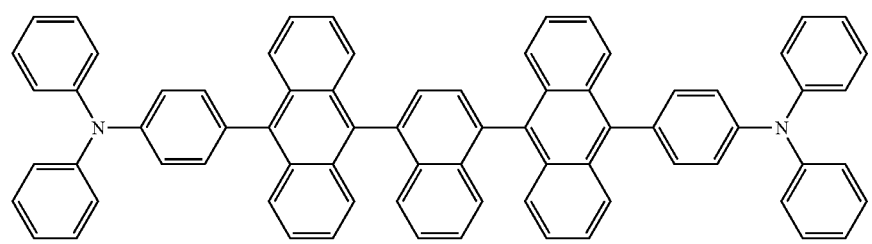

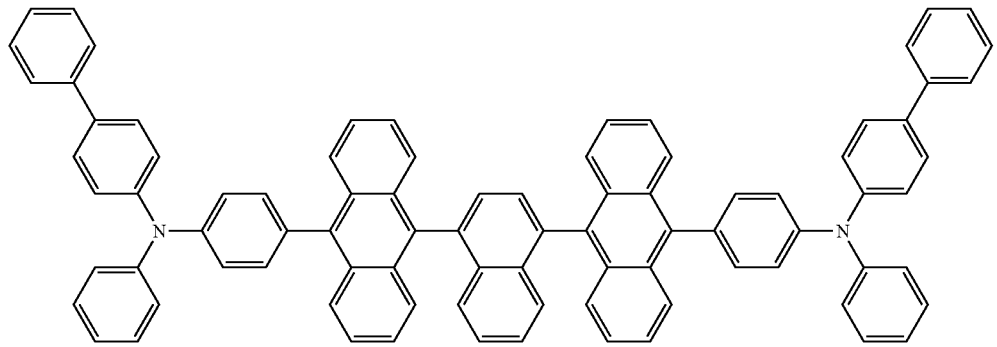
[Compound 38]
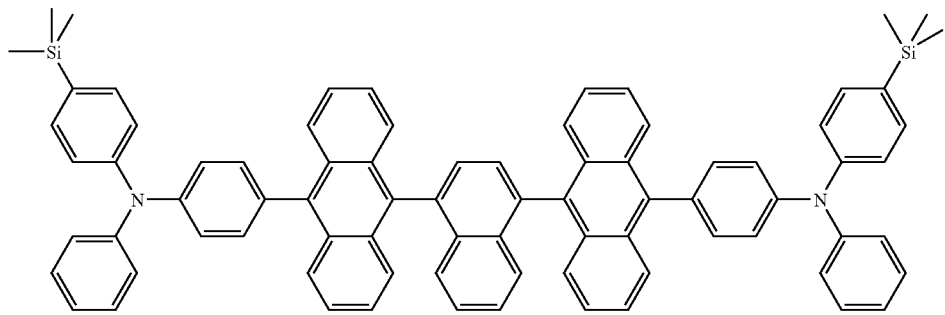
[Compound 39]
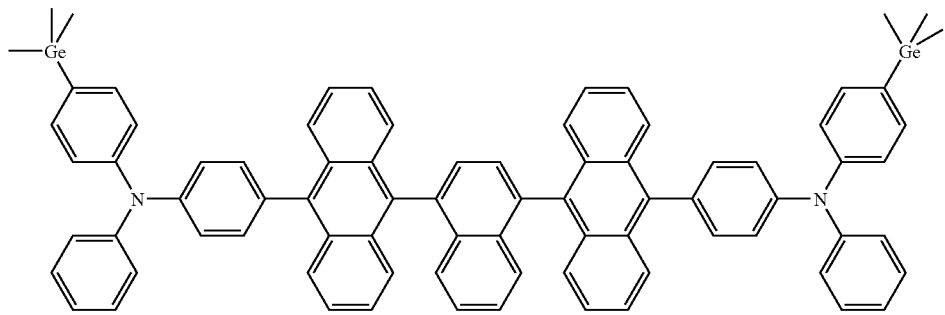
[Compound 40]
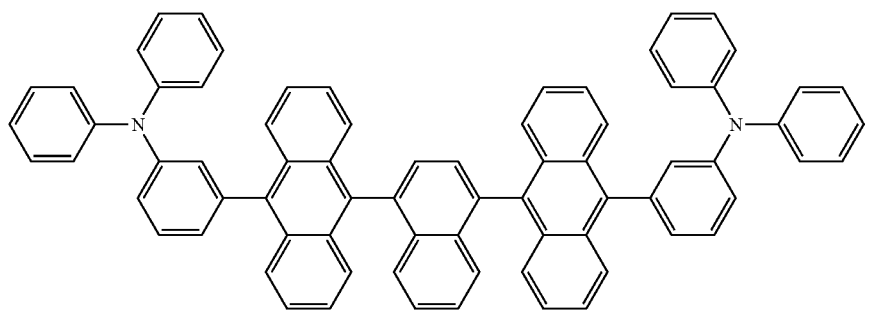
[Compound 41]
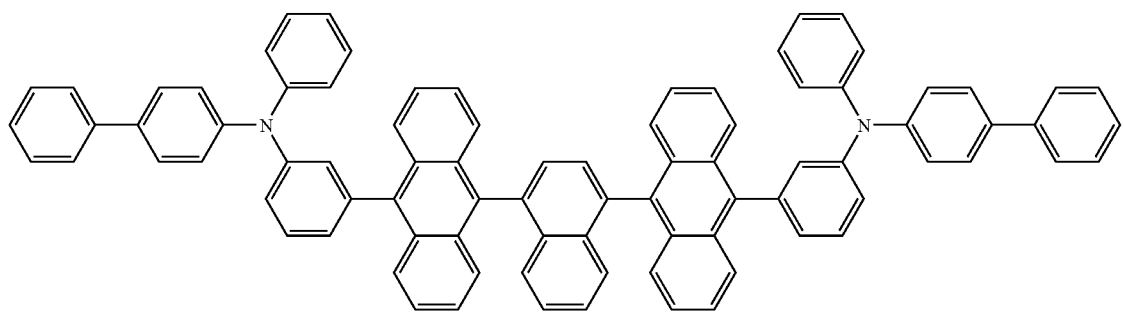
[Compound 42]

[Compound 43]
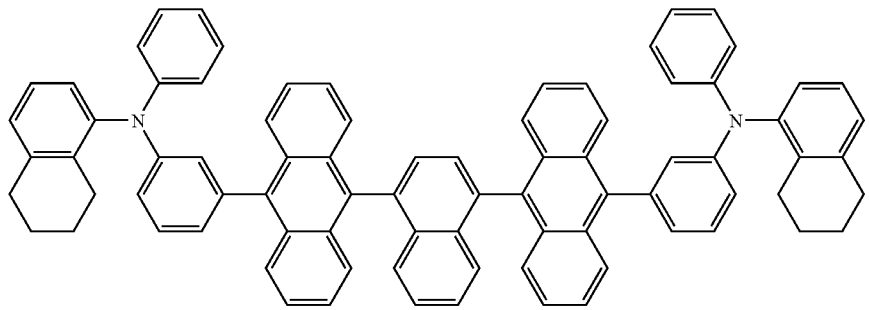
[Compound 44]
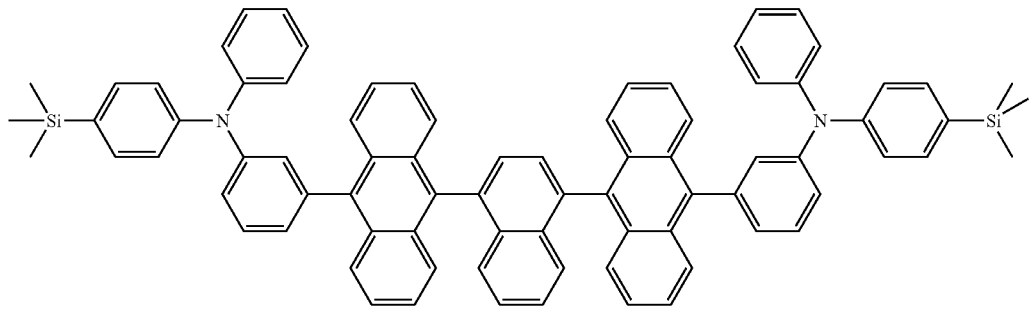
[Compound 45]
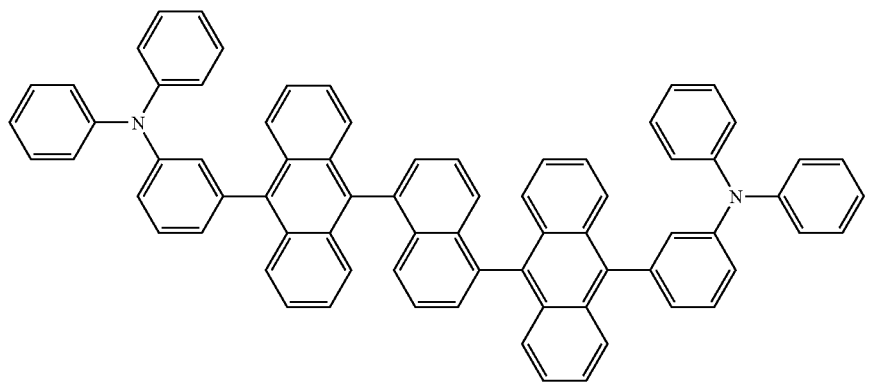
[Compound 46]
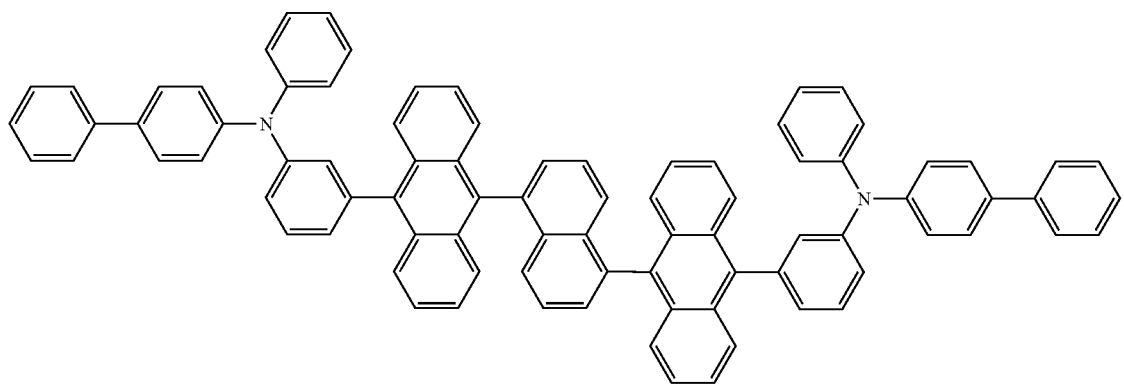

[Compound 47]
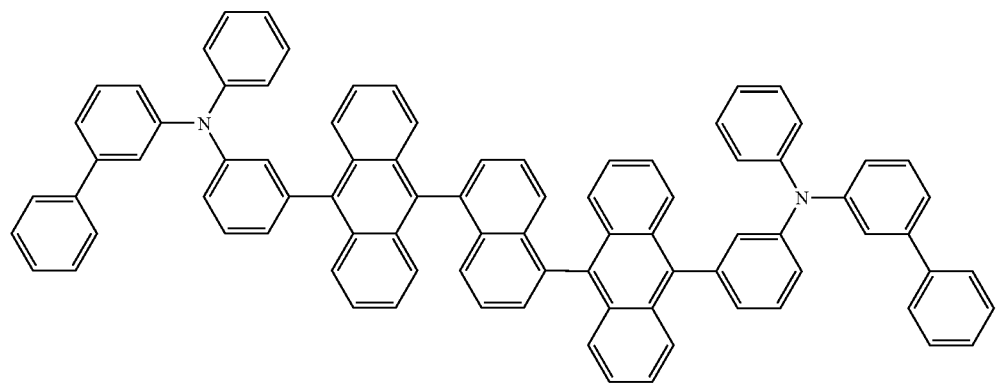
[Compound 48]
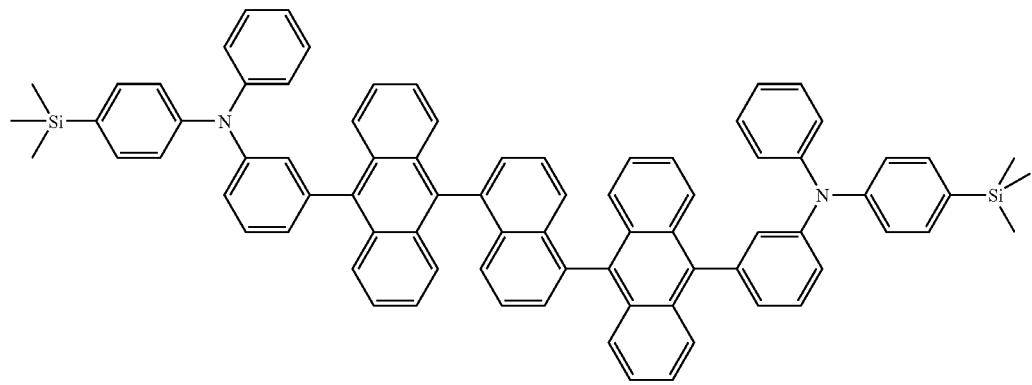
[Compound 49]
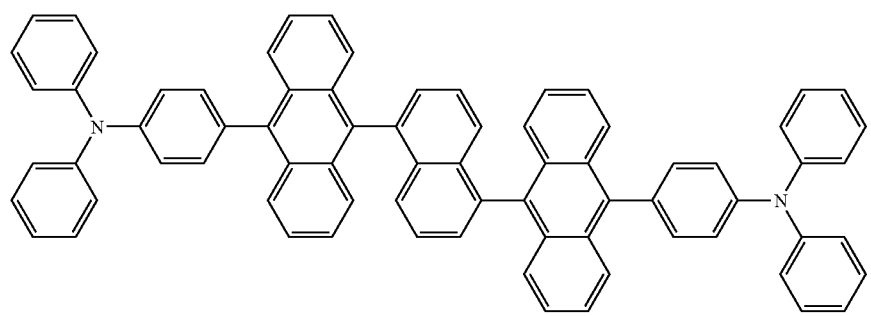
[Compound 50]
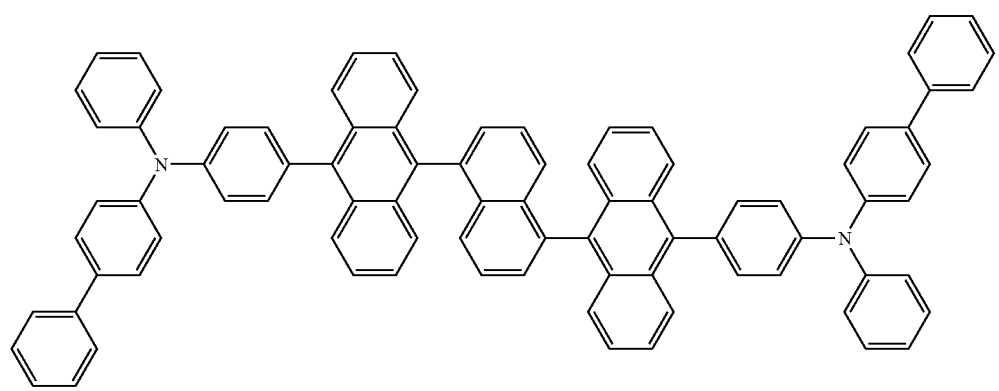

-continued

[Compound 51]

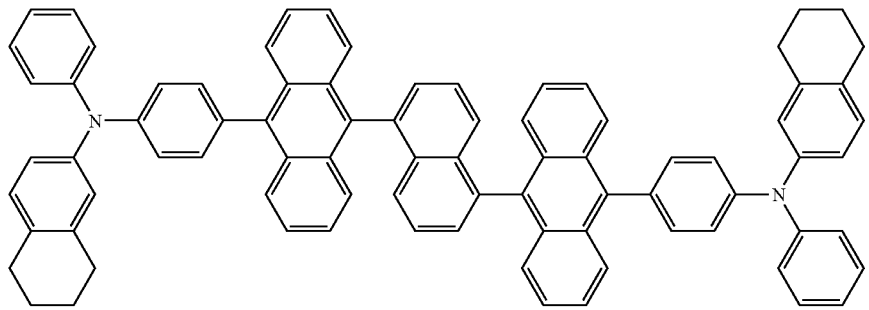

[Compound 52]

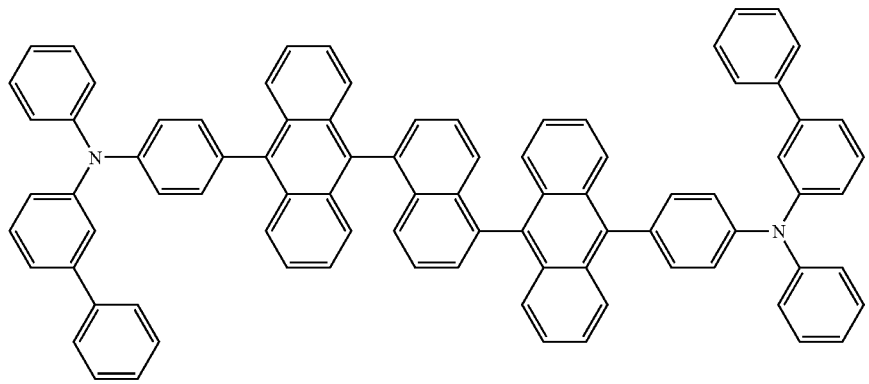

[Compound 53]

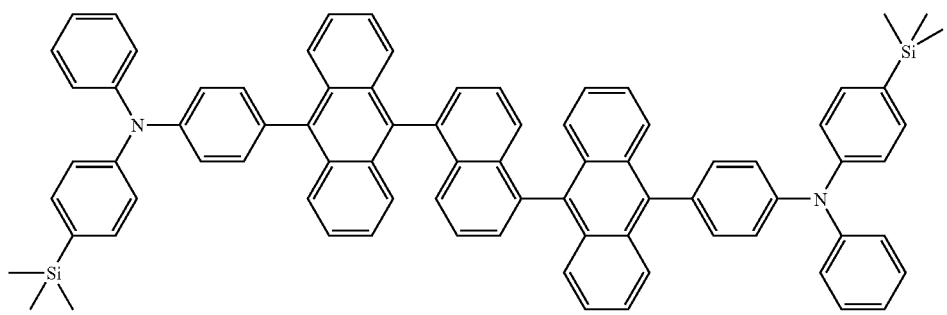

[Compound 54]

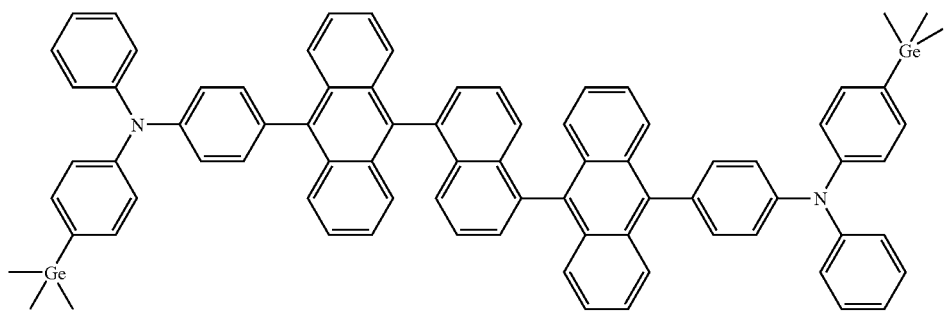

Further, the present invention provides a method for preparing the anthracene derivative represented by the formula 1.

The anthracene derivative according to the present invention can be prepared by reacting a dihalide aryl compound with an arylamine compound in the presence of a palladium catalyst.

Further, the present invention provides an organic electronic device using the compound of the formula 1.

The organic electronic device of the present invention can be prepared by usual methods and materials for preparing an organic electronic device, except that the above-described compounds are used to form at least one organic material layer.

Hereinbelow, the organic light emitting device will be exemplified.

The above-described compounds can function as a hole injecting, hole transporting, electron injecting, electron transporting, or light emitting in the organic light emitting device, and particularly function alone as a light emitting, as well as a light emitting host in combination with an appropriate light emitting dopant or a light emitting dopant in combination with an appropriate light emitting host.

In one embodiment of the present invention, the organic light emitting device may have a structure that comprises a first electrode, a second electrode, and organic material layers interposed therebetween, and can be prepared by usual methods and materials for preparing an organic light emitting device, except that the above-described compound according to the present invention is used to form at least one of the organic material layers in an organic light emitting device. The structure of the organic light emitting device according to the present invention is shown in FIG. 1.

For example, the organic light emitting device according to the present invention can be prepared by depositing a metal, a metal oxide having conductivity, or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon. Alternatively, the organic light emitting device can be prepared by sequentially depositing a cathode material, an organic material layer, and an anode material on a substrate.

The organic material layer may be of a multilayer structure containing a hole injecting layer, a hole transporting layer, a light emitting layer, an electron transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and SnO:Sb; conductive polymers such as poly(3-methylthiophene), poly [3,4-(ethylene-1,2-dioxy)thiophene](PEDT), polypyrrole, and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene, and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is preferably a material having high hole mobility, which can transfer holes from the anode or the hole injecting layer toward the light emitting layer. Specific examples thereof include organic materials of arylamine series, conductive polymers, and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole, and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex ($Alq_3$); complexes including $Alq_3$; organic radical compounds; and hydroxyflavone-metal complexes, but are not limited thereto.

The organic light emitting device according to the invention may be of a front-side, backside or double-sided light emission according to the materials used.

The compound according to the invention can function in an organic electronic device including an organic solar cell, an organic photoconductor, and an organic transistor, according to a principle similar to that applied to the organic light emitting device.

Mode for the Invention

Hereinbelow, the preferred Examples of the present invention will be presented for further understanding the present invention. However, Examples as below are presented merely for illustrative purpose, and thus do not limit the scope of the present invention.

The compound of the formula 1 according to the present invention can be prepared in multi-step chemical reactions. The preparation of the compound is described by way of Examples below. As will be clear in Examples, a certain intermediate compound is first prepared, and then the intermediate compound is used to prepare the compound of the formula 1. Exemplary intermediate compounds are listed below as Compounds A through M. In these compounds, "Br" or "Cl" may be substituted with any other reactive atoms or functional groups.

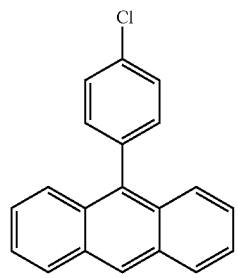

[Compound A]

[Compound B]
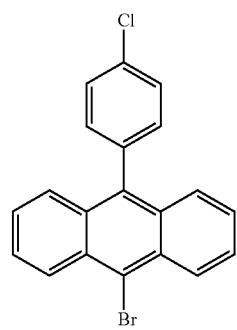
[Compound C]
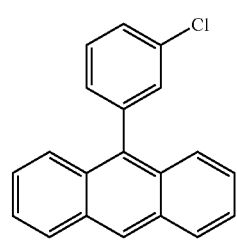
[Compound D]
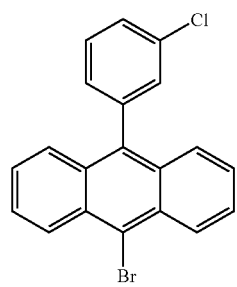
[Compound E]
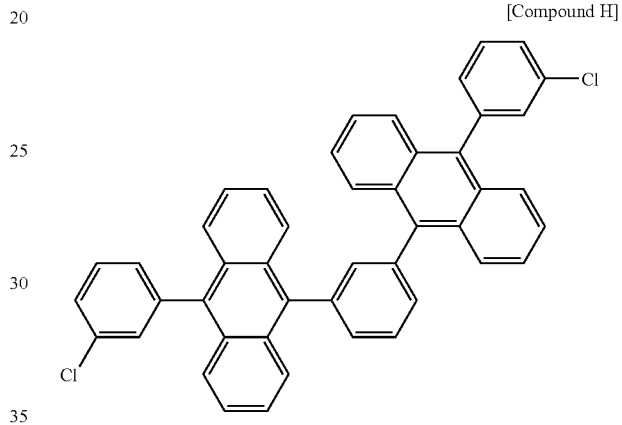
[Compound F]
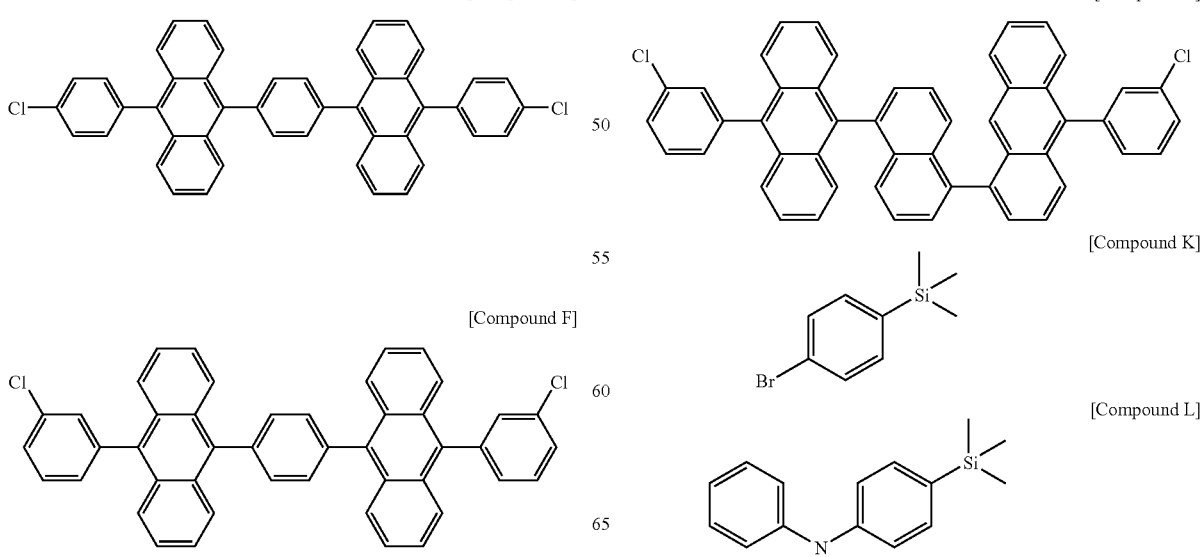
[Compound G]
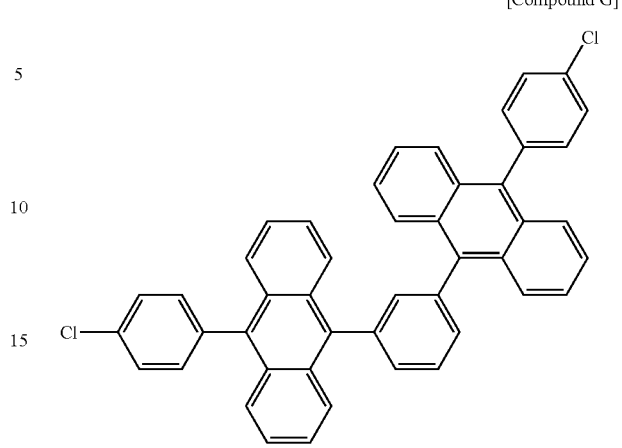
[Compound H]
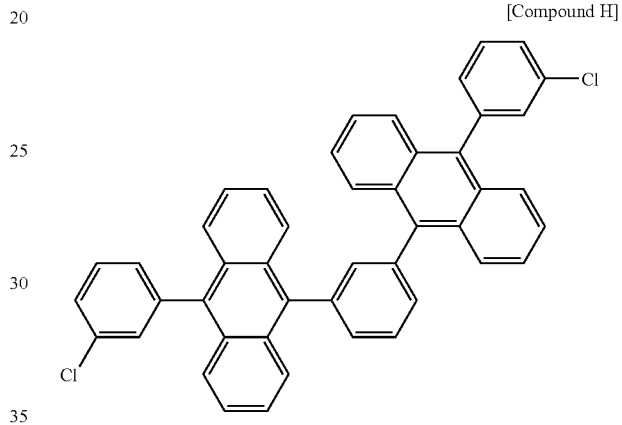
[Compound I]
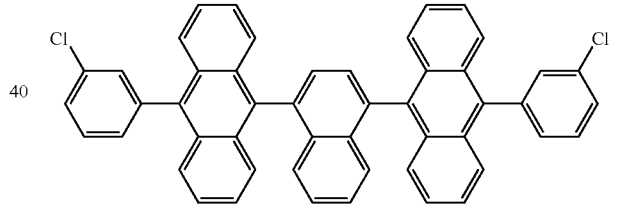
[Compound J]
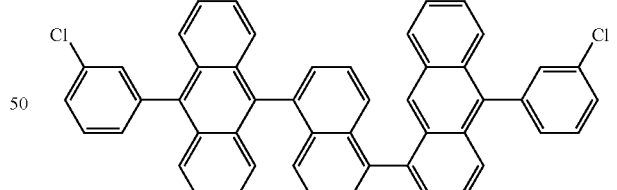
[Compound K]
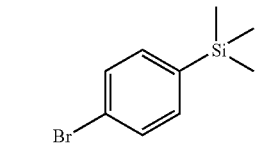
[Compound L]
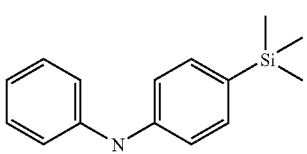

-continued

[Compound M]

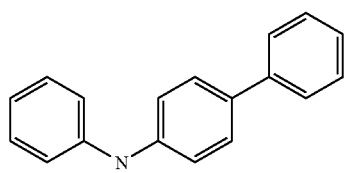

PREPARATION EXAMPLE 1

Preparation of Compound A

Under N$_2$ atmosphere, 9-bromoanthracene (9.18 g, 35.7 mmol), 4-chlorophenylboronic acid (6.7 g, 42.85 mmol), and Pd(PPh$_3$)$_4$ (1.24 g, 0.3 mmol) were added to an aqueous 2 M K$_2$CO$_3$ solution (70 mL) and THF (150 mL). The mixture was refluxed under stirring for about 24 hours. After completing the reaction, the mixture was cooled to room temperature. The organic layer was separated from the reaction mixture, and filtered to obtain a solid. This solid was recrystallized from THF and ethanol to obtain a compound A (9.6 g, 93%).
MS[M]=288

PREPARATION EXAMPLE 2

Preparation of Compound B

Under N$_2$ atmosphere, the compound A (9.6 g, 33.24 mmol) was dissolved in chloroform (100 mL), to which DMF (100 mL) was added, and then NBS (6.5 g, 36.56 mmol) was added dropwise at room temperature. The mixture was stirred for 1 hour. After completing the reaction, the mixture was concentrated, and recrystallized from EtOH to obtain a compound B (11.09 g, 91%).
MS[M]+=367

PREPARATION EXAMPLE 3

Preparation of Compound C

A compound C (9.1 g, 88%) was prepared in the same manner as in Preparation Example 1, except that 3-chlorophenylboronic acid (6.7 g, 42.85 mmol) was used instead of 4-chlorophenylboronic acid (6.7 g, 42.85 mmol) in Preparation Example 1.
MS[M]=288

PREPARATION EXAMPLE 4

Preparation of Compound D

A compound D (10.5 g, 90%) was prepared in the same manner as in Preparation Example 2, except that the compound C (9.1 g, 31.5 mmol) was used instead of the compound A (9.6 g, 33.24 mmol) in Preparation Example 2.
MS[M]=367

PREPARATION EXAMPLE 5

Preparation of Compound E

Under N$_2$ atmosphere, compound B (11.06 g, 30.08 mmol), phenyl-1,4-diboronic acid (1.6 g, 15.04 mmol), and Pd(PPh$_3$)$_4$ (0.52 g, 0.45 mmol) were added to an aqueous 2 M K$_2$CO$_3$ solution (50 mL) and THF (150 mL). The mixture was refluxed under stirring for about 24 hours. After completing the reaction, the mixture was cooled to room temperature. The organic layer was separated from the reaction mixture, and filtered to obtain a solid. This solid was recrystallized from THF and ethanol to obtain a compound E (9.04 g, 92%).
MS[M]=650

PREPARATION EXAMPLE 6

Preparation of Compound F

A compound F (8.78 g, 89%) was prepared in the same manner as in Preparation Example 5, except that the compound D (10.5 g, 28.6 mmol) was used instead of the compound B (11.06 g, 30.08 mmol) in Preparation Example 5.
MS[M]=650

PREPARATION EXAMPLE 7

Preparation of Compound G

A compound G (8.9 g, 91%) was prepared in the same manner as in Preparation Example 5, except that phenyl-1,3-diboronic aid (1.6 g, 15.04 mmol) was used instead of phenyl-1,4-diboronic aid (1.6 g, 15.04 mmol) in Preparation Example 5.
MS[M]=650

PREPARATION EXAMPLE 8

Preparation of Compound H

A compound H (8.8 g, 90%) was prepared in the same manner as in Preparation Example 6, except that phenyl-1,3-diboronic aid (1.6 g, 15.04 mmol) was used instead of phenyl-1,4-diboronic aid (1.6 g, 15.04 mmol) in Preparation Example 6.
MS[M]=650

PREPARATION EXAMPLE 9

Preparation of Compound I

A compound I (10.5 g, 90%) was prepared in the same manner as in Preparation Example 6, except that naphthalene-1,4-diboronic aid (2.35 g, 15.04 mmol) was used instead of phenyl-1,4-diboronic aid (1.6 g, 15.04 mmol) in Preparation Example 6.
MS[M]=700

PREPARATION EXAMPLE 10

Preparation of Compound J

A compound J (10.5 g, 90%) was prepared in the same manner as in Preparation Example 6, except that naphthalene-1,5-diboronic acid (2.35 g, 15.04 mmol) was used instead of phenyl-1,4-diboronic aid (1.6 g, 15.04 mmol) in Preparation Example 6.
MS[M]=700

PREPARATION EXAMPLE 11

Preparation of Compound K

Dibromobenzene (20 g, 84.78 mmol) was dissolved in anhydrous tetrahydrofuran (THF, 200 mL) at room temperature under nitrogen atmosphere. The solution was cooled to −78° C. N-butyllithium (34 mL, 2.5 M pentane solution) was added slowly to the solution at −78° C., and the temperature of the mixture was slowly raised to 0° C. for about 1 hour. To the mixture, chlorotrimethylsilane (13 ml, 101.74 mmol) was added, and the temperature of the mixture was raised to room temperature over 1 hour. After confirmation of completion of the reaction, the mixture was extracted from ethyl acetate, dried over magnesium sulfate, and distilled off under reduced pressure to obtain a compound K (18 g, 93%).
MS[M]=229

PREPARATION EXAMPLE 12

Preparation of Compound L

The compound K (15 g, 65.45 mmol), aniline (6.6 ml, 72 mmol), pd(dba)$_2$ (0.125 g, 0.13 mmol), P(t-Bu)$_3$ (0.04 g, 0.2 mmol), and sodium t-butoxide (1.80 g, 18.7 mmol) were added to toluene (200 mL), and the mixture was refluxed for about 3 hours. After completion of the reaction, the mixture was cooled to room temperature, and the reaction mixture was added to a mixed solution of THF and H$_2$O. The organic layer was separated, dried over MgSO$_4$, and concentrated. The residue was separated by column chromatography to obtain a compound L (15 g, 86%).
MS[M]=143

PREPARATION EXAMPLE 13

Preparation of Compound M

A compound M (13.5 g, 84%) was prepared in the same manner as in Preparation Example 12, except that 4-bromobiphenyl (16.8 g, 72 mmol) was used instead of the compound K (15 g, 65.45 mmol) in Preparation Example 12.
MS(M+)=245

EXAMPLE 1

Preparation of Compound 1

The compound E (5.52 g, 8.5 mmol), diphenylamine (3.45 g, 20.4 mmol), pd(dba)$_2$ (0.097 g, 0.17 mmol), P(t-Bu)$_3$ (0.05 g, 0.255 mmol), and sodium t-butoxide (2.45 g, 25.5 mmol) were added to toluene (100 mL), and the mixture was refluxed for about 2 hours. After completion of the reaction, the mixture was cooled to room temperature, and the reaction mixture was added to a mixed solution of THF and H$_2$O. The organic layer was separated, dried over MgSO$_4$, and concentrated. The residue was separated by column chromatography to obtain a compound 1 (4.52 g, 58%).
MS[M]=916

EXAMPLE 2

Preparation of Compound 11

A compound 11 (5.9 g, 65%) was prepared in the same manner as in Example 1, except that the compound F (5.52 g, 8.5 mmol) was used instead of the compound E (5.52 g, 8.5 mmol), and the compound M (4.99 g, 20.4 mmol) was used instead of diphenylamine (3.45 g, 20.4 mmol) in Example 1.
MS[M]=1068

EXAMPLE 3

Preparation of Compound 14

A compound 14 (5.9 g, 65%) was prepared in the same manner as in Example 1, except that the compound L (2.91 g, 20.4 mmol) was used instead of the compound M (4.99 g, 20.4 mmol) in Example 2.
MS[M]=1060

EXAMPLE 4

Preparation of Compound 20

A compound 20 (5.5 g, 60%) was prepared in the same manner as in Example 1, except that the compound H (5.52 g, 8.5 mmol) was used instead of the compound E (5.52 g, 8.5 mmol), and the compound M (4.99 g, 20.4 mmol) was used instead of diphenylamine (3.45 g, 20.4 mmol) in Example 1.
MS[M]=1068

EXAMPLE 5

Preparation of Compound 24

A compound 24 (4.7 g, 52%) was prepared in the same manner as in Example 1, except that the compound L (2.91 g, 20.4 mmol) was used instead of the compound M (4.99 g, 20.4 mmol) in Example 4.
MS[M]=1060

EXAMPLE 6

Preparation of Compound 33

A compound 33 (4.7 g, 52%) was prepared in the same manner as in Example 1, except that the compound G (5.52 g, 8.5 mmol) was used instead of the compound E (5.52 g, 8.5 mmol), and the compound L (2.91 g, 20.4 mmol) was used instead of diphenylamine (3.45 g, 20.4 mmol) in Example 1.
MS[M]=1060

EXAMPLE 7

Preparation of Compound 44

A compound 44 (4.5 g, 48%) was prepared in the same manner as in Example 1, except that the compound I (5.96 g, 8.5 mmol) was used instead of the compound E (5.52 g, 8.5 mmol), and the compound L (2.91 g, 20.4 mmol) was used instead of diphenylamine (3.45 g, 20.4 mmol) in Example 1.
MS[M]=1110

EXAMPLE 8

Preparation of Compound 46

A compound 46 (5.1 g, 54%) was prepared in the same manner as in Example 1, except that the compound J (5.96 g, 8.5 mmol) was used instead of the compound E (5.52 g, 8.5 mmol), and the compound M (4.99 g, 20.4 mmol) was used instead of diphenylamine (3.45 g, 20.4 mmol) in Example 1.
MS[M]=1118

EXAMPLE 9

Preparation of Compound 48

A compound 48 (4.5 g, 48%) was prepared in the same manner as in Example 1, except that the compound L (2.91 g, 20.4 mmol) was used instead of the compound M (4.99 g, 20.4 mmol) in Example 8.

MS[M]=1110

EXPERIMENTAL EXAMPLE 1

A glass substrate (Corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone, and methanol. The resultant product was dried, and then transported to a plasma washing machine. Using an oxygen plasma, the substrate was washed for 5 minutes and then transported to a vacuum depositing machine.

On the ITO electrode, 3,6-bis-2-naphthylphenylamino-N-[4-(2-naphthylphenyl)aminophenyl]carbazole (800 Å), and 4,4'-bis[N-(1-naphthyl)-N-phenylamino]biphenyl (NPB) (300 Å) were sequentially coated by thermal vacuum deposition to form a hole injecting layer and a hole transporting layer, respectively.

The compound 20 (4 wt %) as prepared in Example 4 was deposited thereon with the following compound N (300 Å) to form a light emitting layer, and then 9,10-bis-2-naphthyl-2-[4-(N-phenylbenzoimidazoyl)phenyl]anthracene (300 Å) was coated by thermal vacuum deposition to form an electron transporting layer.

Lithium fluoride (LiF) and aluminum were sequentially deposited on the electron transporting layer to thicknesses of 12 Å and 2,000 Å respectively, to form a cathode, thereby obtaining an organic light emitting device.

In the above process, the deposition rate of the organic material was maintained at 0.4 to 0.7 Å/sec, and the deposition rate of lithium fluoride on the cathode was maintained at 0.3 Å/sec, and the deposition rate of aluminum was maintained at 2 Å/sec. The degree of vacuum upon deposition was maintained at $2 \times 10^{-7}$ to $5 \times 10^{-8}$ torr.

When a forward electric field of 8.0 V was applied to the organic light emitting device as prepared above, blue light emission of 8.5 cd/A was observed with x=0.138, and y=0.295 based on the 1931 CIE color coordinate at a current density of 100 mA/cm².

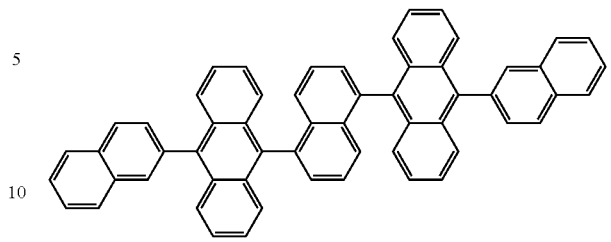

[Compound N]

EXPERIMENTAL EXAMPLE 2

An organic light emitting device was prepared in the same manner as in Experimental Example 1, except that the compound 24 was used instead of the compound 20 in Experimental Example 1.

When a forward electric field of 8.1 V was applied to the organic light emitting device as prepared above, blue light emission of 8.7 cd/A was observed with x=0.137, and y=0.288 based on the 1931 CIE color coordinate at a current density of 100 mA/cm².

EXPERIMENTAL EXAMPLE 3

An organic light emitting device was prepared in the same manner as in Experimental Example 1, except that the compound 33 was used instead of the compound 20 in Experimental Example 1.

When a forward electric field of 8.1 V was applied to the organic light emitting device as prepared above, blue light emission of 8.6 cd/A was observed with x=0.134, and y=0.289 based on the 1931 CIE color coordinate at a current density of 100 mA/cm².

EXPERIMENTAL EXAMPLE 4

An organic light emitting device was prepared in the same manner as in Experimental Example 1, except that the compound 46 was used instead of the compound 20 in Experimental Example 1.

When a forward electric field of 8.3 V was applied to the organic light emitting device as prepared above, blue light emission of 8.5 cd/A was observed with x=0.134, and y=0.298 based on the 1931 CIE color coordinate at a current density of 100 mA/cm².

EXPERIMENTAL EXAMPLE 5

An organic light emitting device was prepared in the same manner as in Experimental Example 1, except that the compound 48 was used instead of the compound 20 in Experimental Example 1.

When a forward electric field of 8.4 V was applied to the organic light emitting device as prepared above, blue light emission of 8.6 cd/A was observed with x=0.137, and y=0.301 based on the 1931 CIE color coordinate at a current density of 100 mA/cm².

The invention claimed is:

1. An anthracene derivative represented by the following formula 1:

[Formula 1]

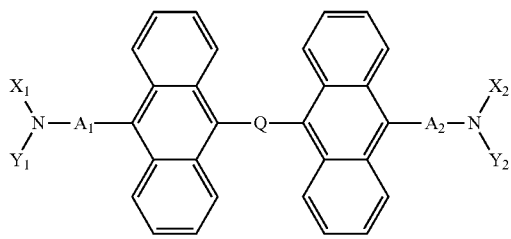

wherein $X_1$, $X_2$, $Y_1$, and $Y_2$ are the same or different from each other, and are each independently a $C_6$ to $C_{20}$ aryl group which is substituted with at least one selected from the group consisting of —SiRR'R", and —GeRR'R"; a $C_5$ to $C_{20}$ heterocyclic group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_6$ to $C_{20}$ arylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_5$ to $C_{20}$ heterocyclic group, —BRR', —SiRR'R", and —GeRR'R"; or a $C_2$ to $C_{20}$ alkylene group which is combined with a $C_6$ to $C_{20}$ aryl group to form a fused ring, wherein R, R' and R" are the same or different from each other, and are each independently hydrogen, a $C_1$ to $C_{20}$ alkyl group, a $C_3$ to $C_{20}$ cycloalkyl group, a $C_6$ to $C_{20}$ aryl group, or $C_5$ to $C_{20}$ heterocyclic group, Q is

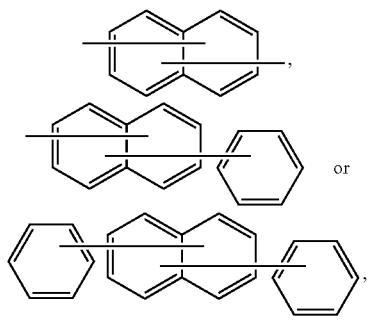

and $A_1$ and $A_2$ are the same or different from each other, and are each independently

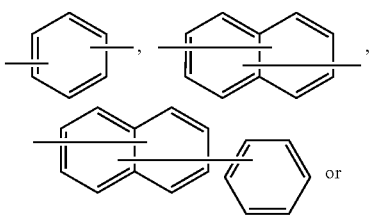

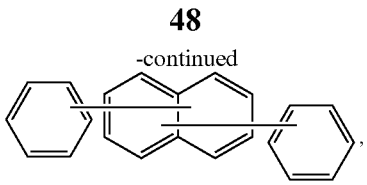

with a proviso that $X_1$ and $Y_1$ are different from each other and $X_2$ and $Y_2$ are different from each other.

2. The anthracene derivative according to claim 1, wherein in the formula 1, $X_1$, $X_2$, $Y_1$, and $Y_2$ are each independently phenyl, naphthyl, biphenyl, fluorenyl, anthracenyl, tetracenyl, pentacenyl, terphenyl, tetralinyl, stilbenyl, perylenyl, pyrenyl, phenanthrenyl, triphenylenyl, crycenyl, or pyridyl, which is substituted with at least one selected from the group consisting of —SiRR'R", and —GeRR'R"; or a $C_2$ to $C_{20}$ alkylene group which is combined with phenyl or naphthyl to form a fused ring, wherein R, R' and R" are the same or different from each other, and are each independently a $C_1$ to $C_{20}$ alkyl group.

3. The anthracene derivative according to claim 1, wherein in the formula 1,

Q is selected from the group consisting of the following structural formulae:

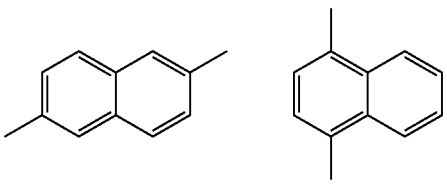

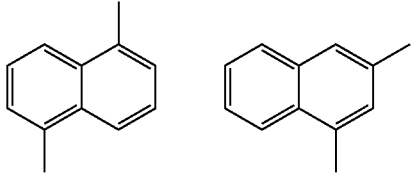

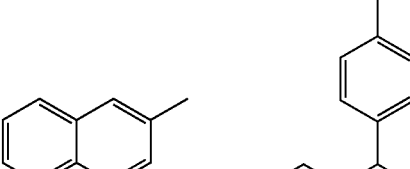

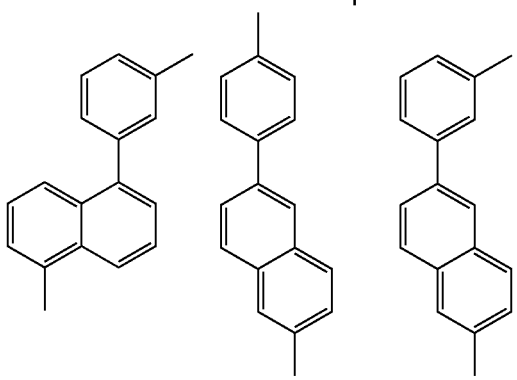

-continued
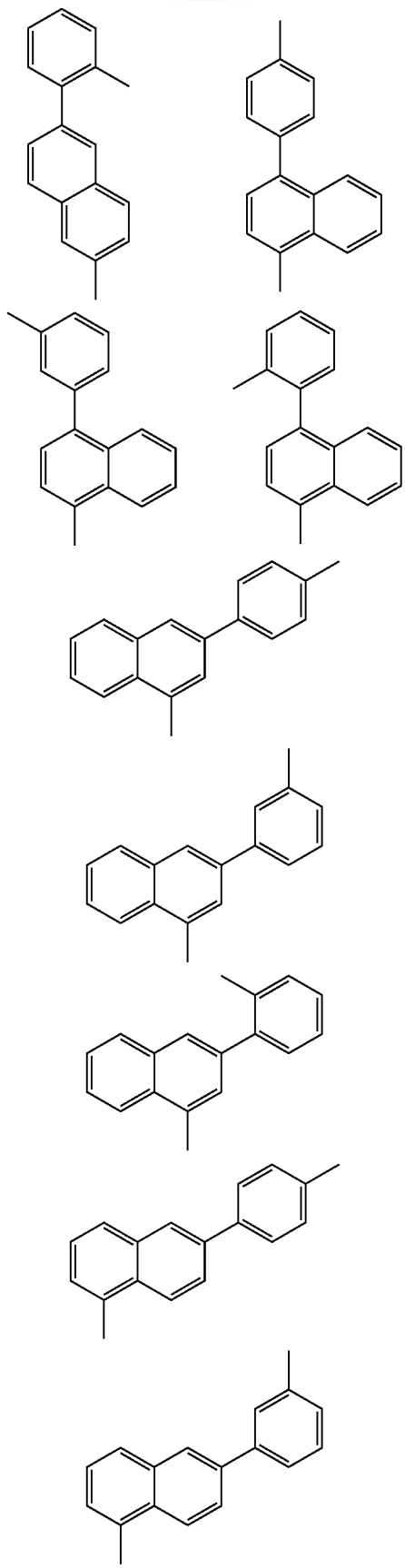
-continued
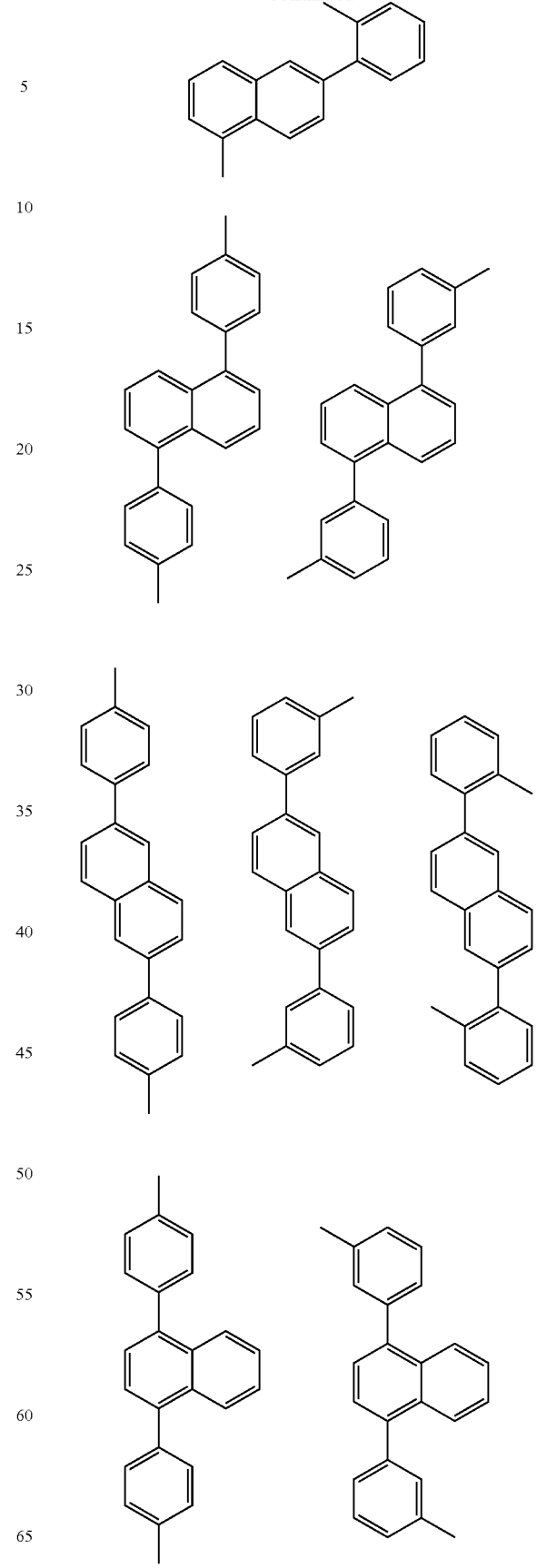

-continued
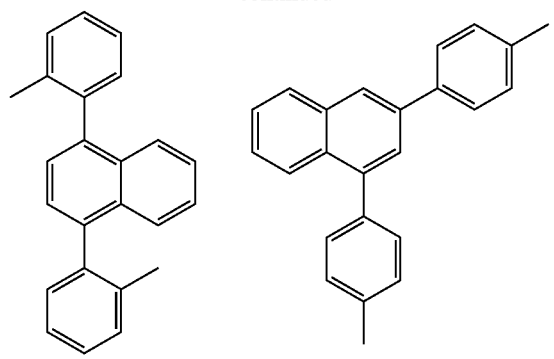
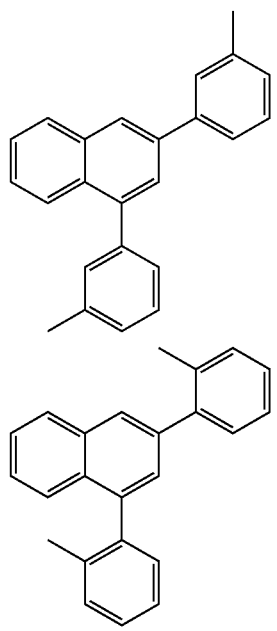
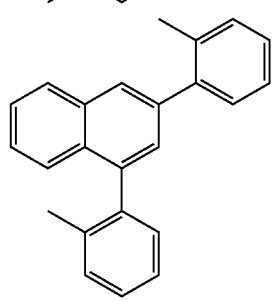
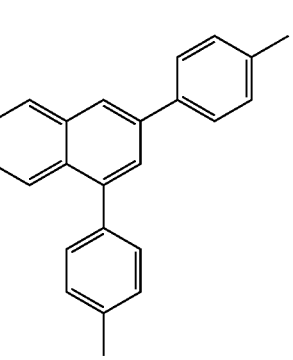
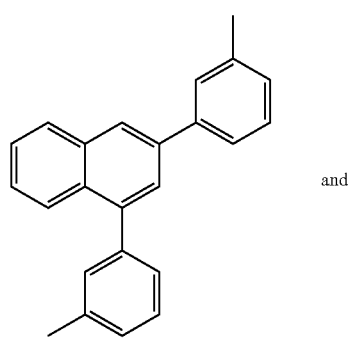
and
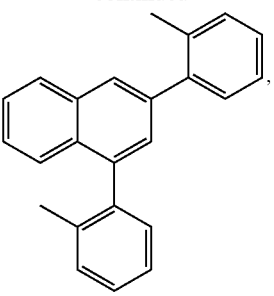
$A_1$ and $A_2$ are the same or different from each other, and are each independently a group selected from the group consisting of the following structural formulae:
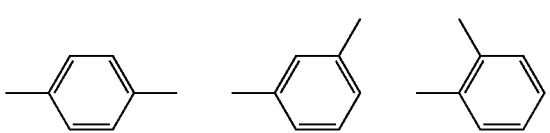
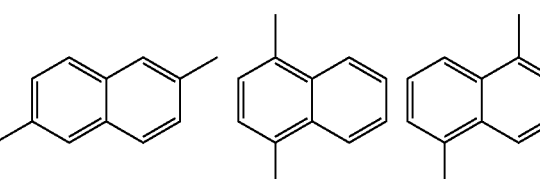
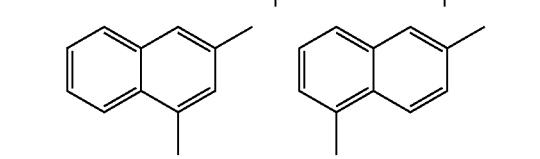
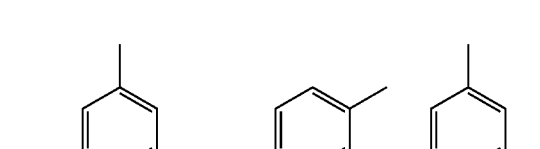
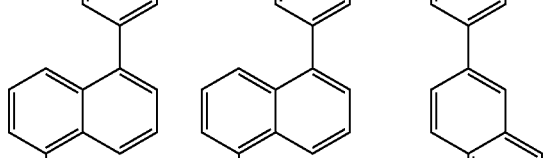
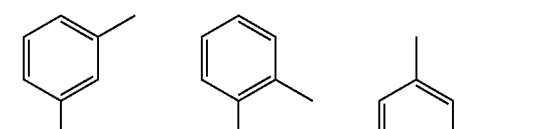
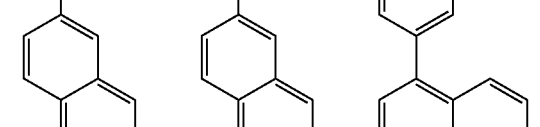

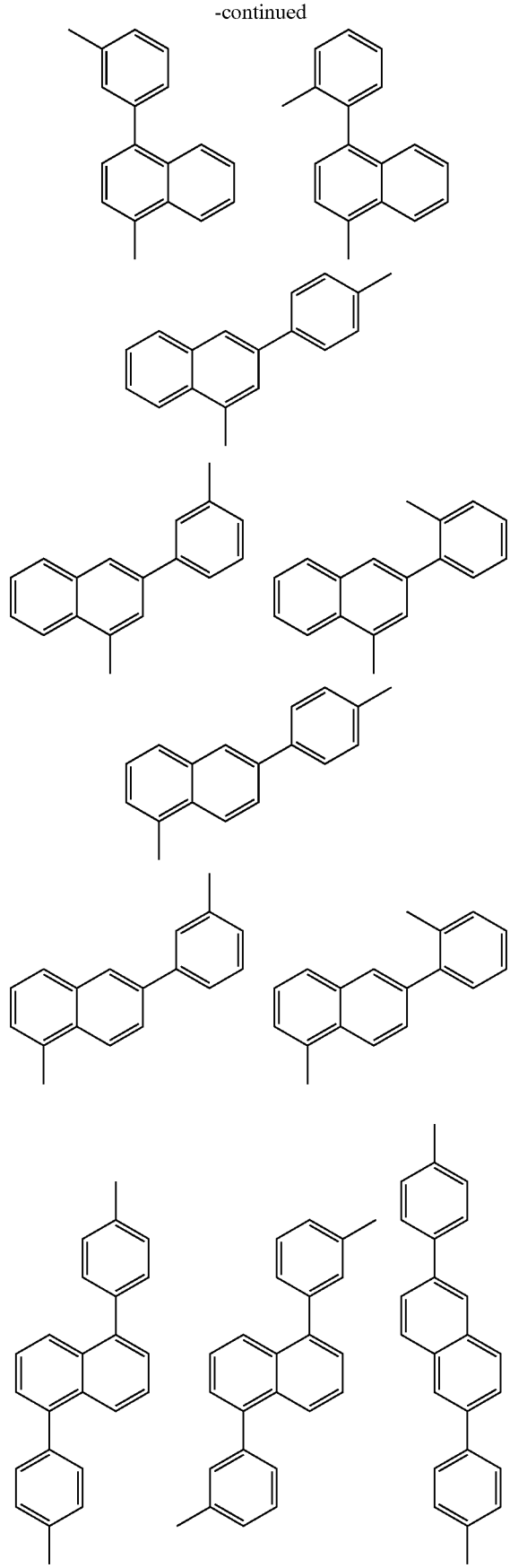
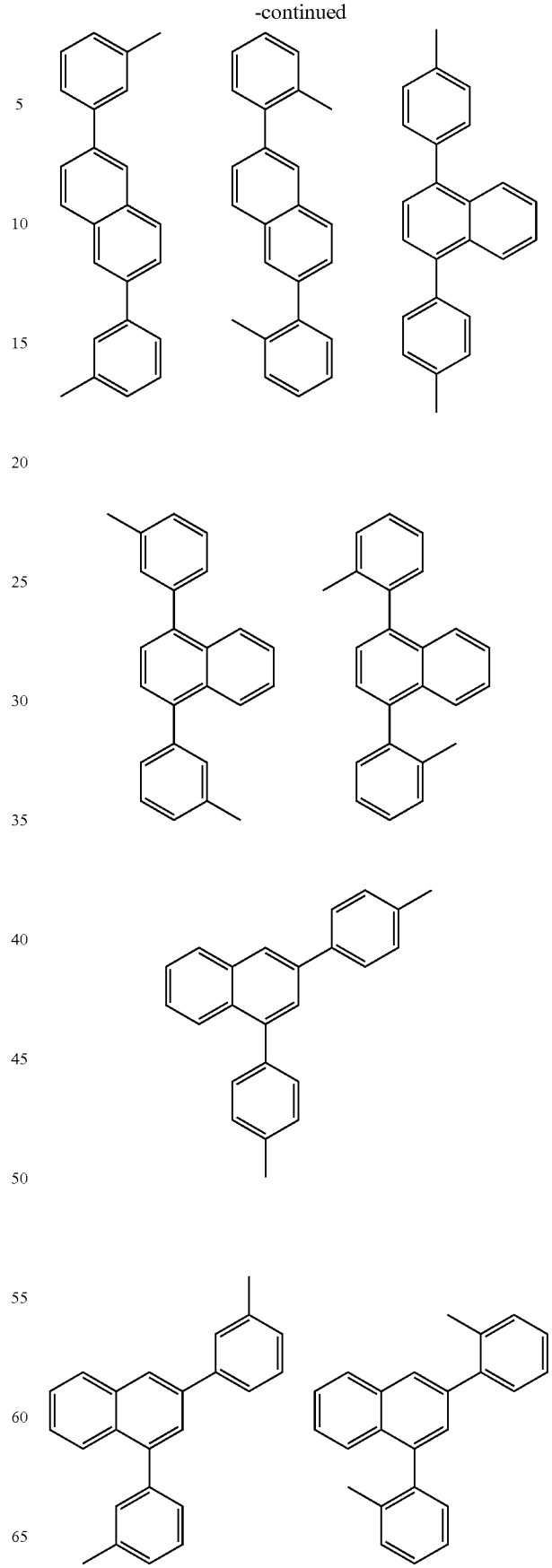

-continued
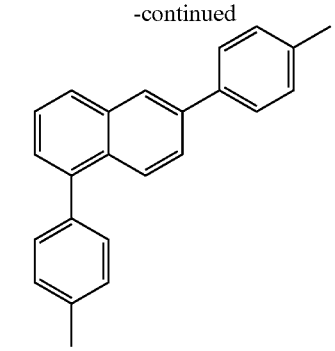
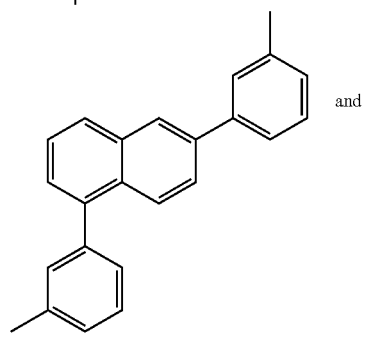
and
-continued
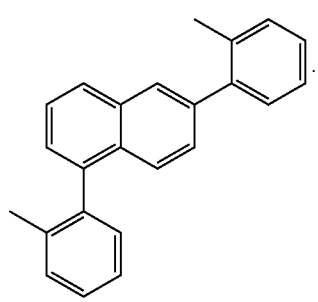
4. The anthracene derivative according to claim 1, wherein the compound of the formula 1 is selected from the group consisting of the following structural formulae:
[Compound 39]
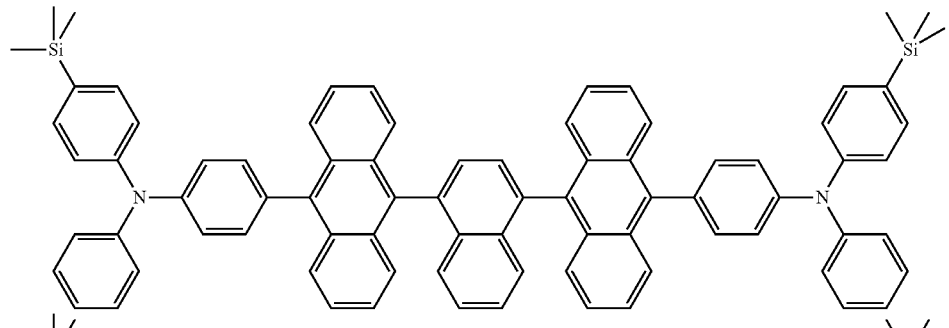
[Compound 40]
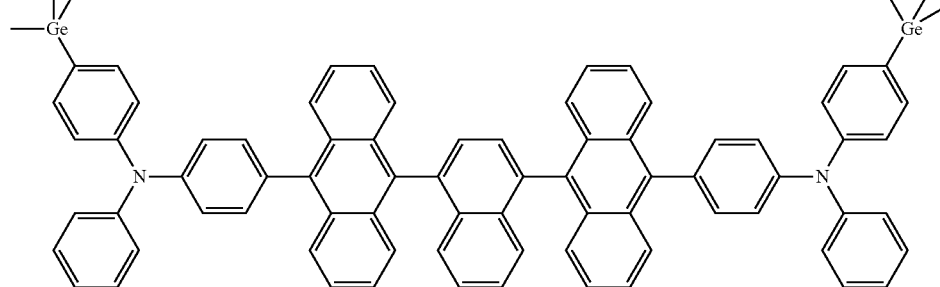
[Compound 43]
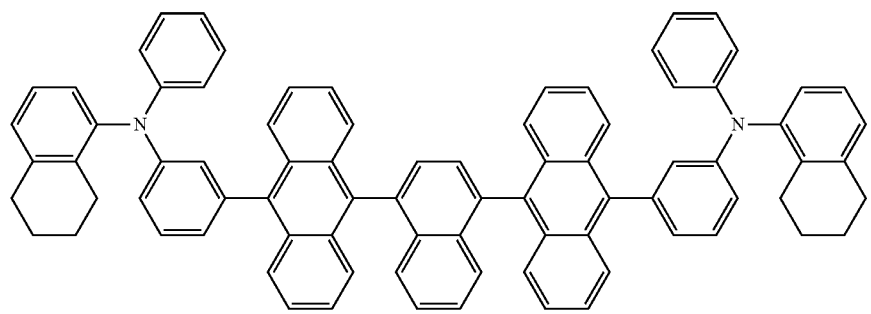

[Compound 44]
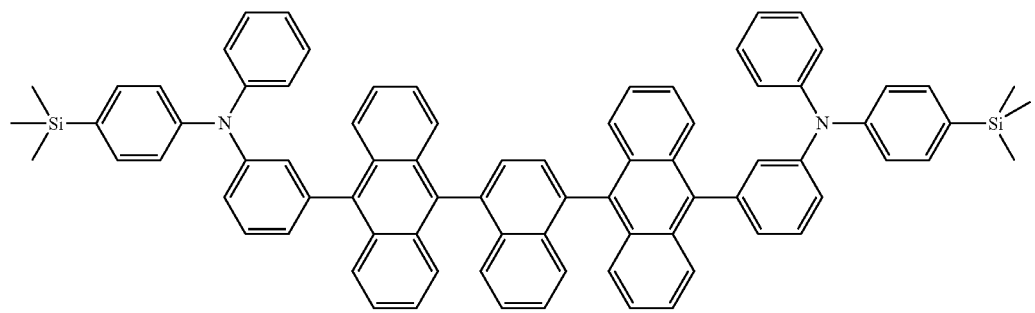
[Compound 48]
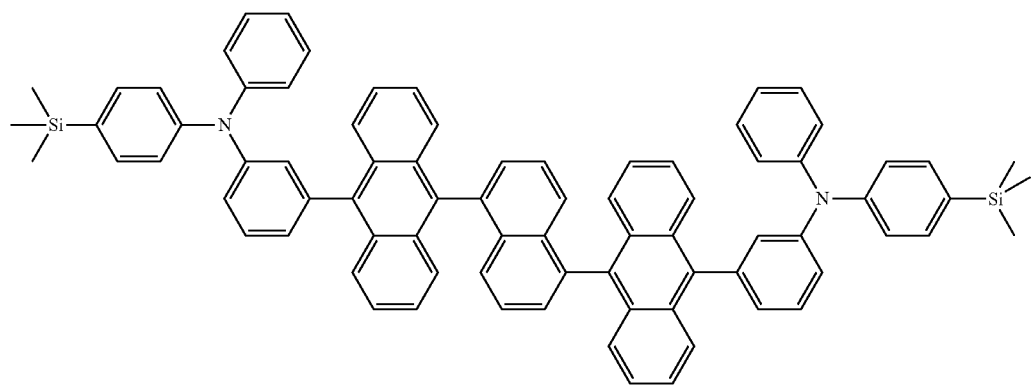
[Compound 51]
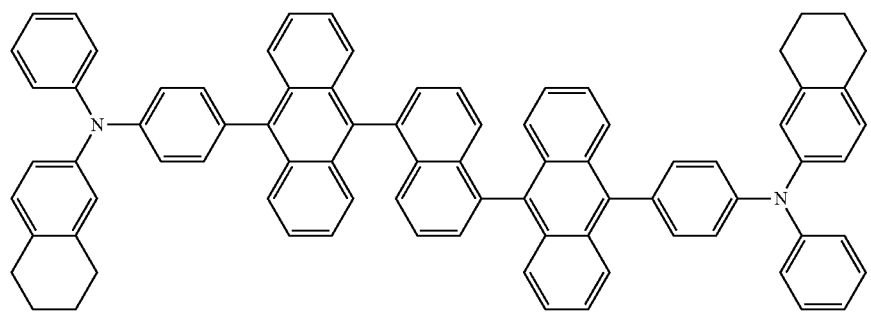
[Compound 53]
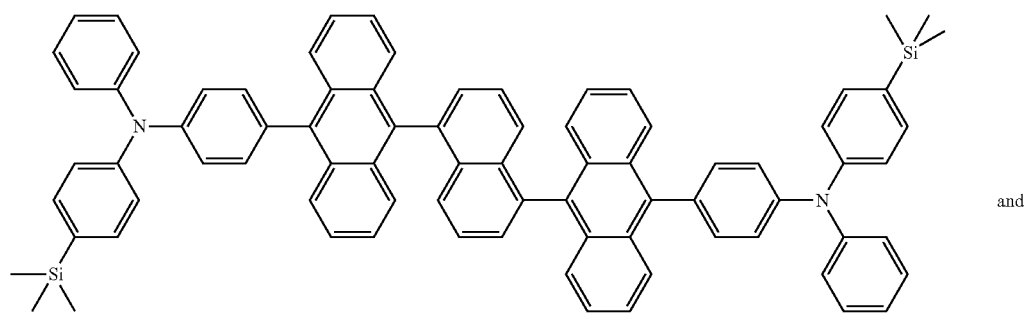
and -continued

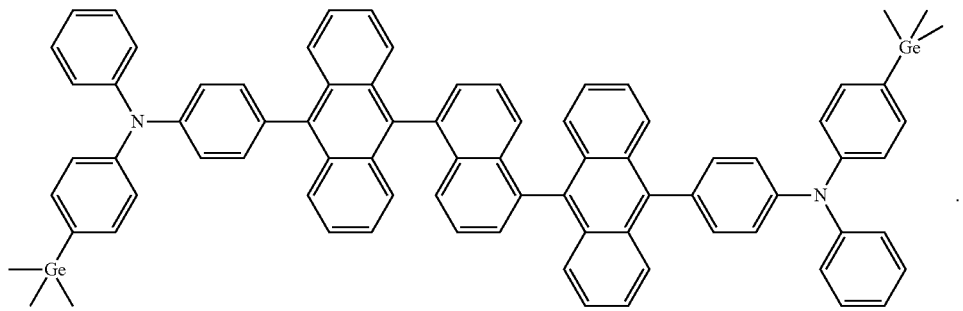

[Compound 54]

5. An organic electronic device comprising a first electrode, a second electrode, and at least one organic material layer interposed between the first electrode and the second electrode, wherein at least one layer of the organic material layers comprises the anthracene derivative of the formula 1 according to any one of claims 1 to 4.

6. The organic electronic device according to claim 5, wherein the organic electronic device is selected from the group consisting of an organic light emitting device, an organic solar cell, an organic photoconductor (OPC), and an organic transistor.

7. The organic electronic device according to claim 6, wherein the organic electronic device is an organic light emitting device, the organic material layer comprises at least one of a hole injecting layer, a hole transporting layer, and a hole injecting and hole transporting layer, and at least one of the layers comprises the the anthracene derivative of the formula 1.

8. The organic electronic device according to claim 6, wherein the organic electronic device is an organic light emitting device, the organic material layer comprises a light emitting layer, and the light emitting layer comprises the the anthracene derivative of the formula 1.

9. The organic electronic device according to claim 6, wherein the organic electronic device is an organic light emitting device, the organic material layer comprises an electron transporting layer, and the electron transporting layer comprises the the anthracene derivative of the formula 1.

* * * * *